US011267924B2

(12) United States Patent
Dhal et al.

(10) Patent No.: US 11,267,924 B2
(45) Date of Patent: Mar. 8, 2022

(54) CROSSLINKED POLYDIALLYMINE COPOLYMERS FOR THE TREATMENT OF TYPE 2 DIABETES

(71) Applicant: GENZYME CORPORATION, Cambridge, MA (US)

(72) Inventors: Pradeep K. Dhal, Westford, MA (US); Robert J. Miller, East Bridgewater, MA (US); Steven C. Polomoscanik, Methuen, MA (US); Philip Just Larsen, Klampenborg (DK); Thomas Huebschle, Münzenberg (DE); Thorsten Schmidt, Eschborn (DE); Ian Davison, Kedington (GB); Peter D. McDonnell, Bury St. Edmunds (GB); Chinyere Agbugba, Haverhill (GB)

(73) Assignee: GENZYME CORPORATION, Bridgewater, NJ (US)

( * ) Notice: Subject to any disclaimer, the term of this patent is extended or adjusted under 35 U.S.C. 154(b) by 1224 days.

(21) Appl. No.: 14/971,424

(22) Filed: Dec. 16, 2015

(65) Prior Publication Data

US 2016/0177019 A1 Jun. 23, 2016

Related U.S. Application Data

(60) Provisional application No. 62/093,751, filed on Dec. 18, 2014.

(51) Int. Cl.
*C08F 226/04* (2006.01)
*C08F 299/00* (2006.01)
(Continued)

(52) U.S. Cl.
CPC .......... *C08F 299/00* (2013.01); *A61K 31/785* (2013.01); *A61K 31/787* (2013.01);
(Continued)

(58) Field of Classification Search
CPC ...... C08F 299/00; C08F 226/04; C08F 26/04; A61K 31/787
See application file for complete search history.

(56) References Cited

U.S. PATENT DOCUMENTS 2,456,428 A 12/1948 Parker
3,104,205 A 9/1963 Hainer et al.
(Continued)

FOREIGN PATENT DOCUMENTS

AU 480922 A1 2/1977
AU 689797 B2 4/1998
(Continued)

OTHER PUBLICATIONS

Vivekanandam, T.S. et al, "Sonochemical cyclopolymerization of diallylamine", 2000, European Polymer Journal, 36, 385-392 (Year: 2000).*
(Continued)

*Primary Examiner* — Ling Siu Choi
*Assistant Examiner* — David L Miller
(74) *Attorney, Agent, or Firm* — Nicholas P. Triano, III

(57) ABSTRACT

Polydiallylamine copolymers are copolymers comprising monomers of polydiallylamine and either polyvinlyamine or polyallylamine. Polydiallylamine copolymers are often crosslinked. The polydiallyamine copolymers are useful as pharmaceutical compositions and may be used in the treatment of type 2 diabetes and for mitigating the complications of type 2 diabetes.

7 Claims, 11 Drawing Sheets

General Synthesis Scheme for Crosslinked Polydiallylamine-Polyvinlyamine (PDA-PVAm) Copolymers

(51) Int. Cl.

| | |
|---|---|
| ***C08F 8/00*** | (2006.01) |
| ***A61K 31/785*** | (2006.01) |
| ***A61K 45/06*** | (2006.01) |
| ***A61K 31/787*** | (2006.01) |
| *C08F 26/04* | (2006.01) |

(52) U.S. Cl.
CPC ................ *A61K 45/06* (2013.01); *C08F 8/00* (2013.01); *C08F 226/04* (2013.01); *C08F 26/04* (2013.01)

(56) References Cited

U.S. PATENT DOCUMENTS

| | | | |
|---|---|---|---|
| 3,119,742 | A | 1/1964 | Heimlich et al. |
| 3,293,195 | A | 12/1966 | Greer |
| 3,308,020 | A | 3/1967 | Tennant et al. |
| 3,332,841 | A | 7/1967 | Ainsworth et al. |
| 3,492,397 | A | 1/1970 | David et al. |
| 3,538,214 | A | 11/1970 | Gerald et al. |
| 3,624,209 | A | 11/1971 | Granatek et al. |
| 3,980,770 | A | 9/1976 | Ingelman et al. |
| 4,060,598 | A | 11/1977 | Groppenbacher et al. |
| 4,071,478 | A | 1/1978 | Shen et al. |
| 4,143,130 | A | 3/1979 | Imondi et al. |
| 4,173,626 | A | 11/1979 | Dempski et al. |
| 4,181,718 | A | 1/1980 | Mason et al. |
| 4,183,918 | A | 1/1980 | Asher et al. |
| 4,205,064 | A | 5/1980 | Wagner et al. |
| 4,247,393 | A | 1/1981 | Wallace |
| 4,344,993 | A | 8/1982 | Schmidt et al. |
| 4,439,419 | A | 3/1984 | Vecchio |
| 4,504,640 | A | 3/1985 | Harada et al. |
| 4,605,701 | A | 8/1986 | Harada et al. |
| 4,631,305 | A | 12/1986 | Guyer et al. |
| 4,895,621 | A | 1/1990 | Hassler |
| 5,053,423 | A | 10/1991 | Liu |
| 5,055,197 | A | 10/1991 | Albright et al. |
| 5,108,767 | A | 4/1992 | Mulchandani et al. |
| 5,136,032 | A | 8/1992 | Nagamatsu et al. |
| 5,302,531 | A | 4/1994 | Bauer |
| 5,374,422 | A | 12/1994 | St. Pierre et al. |
| 5,414,068 | A | 5/1995 | Bliem et al. |
| 5,428,112 | A | 6/1995 | Ahlers et al. |
| 5,430,110 | A | 7/1995 | Ahlers et al. |
| 5,462,730 | A | 10/1995 | McTaggart et al. |
| 5,487,888 | A | 1/1996 | Mandeville et al. |
| 5,496,545 | A | 3/1996 | Holmes-Farley et al. |
| 5,667,775 | A | 9/1997 | Holmes-Farley et al. |
| 5,702,696 | A | 12/1997 | Mandeville et al. |
| 5,985,938 | A | 11/1999 | Holmes-Farley et al. |
| 6,083,495 | A | 7/2000 | Holmes-Farley et al. |
| 6,177,478 | B1 | 1/2001 | Holmes-Farley et al. |
| 6,274,713 | B1 | 8/2001 | Sieving et al. |
| 6,281,252 | B1 | 8/2001 | Holmes-Farley et al. |
| 6,335,402 | B1 | 1/2002 | Mihan et al. |
| 6,365,186 | B1 * | 4/2002 | Huval .................. A61K 31/785 424/486 |
| 6,500,527 | B2 | 12/2002 | Millera |
| 6,509,013 | B1 | 1/2003 | Holmes-Farley et al. |
| 6,566,407 | B2 | 5/2003 | Holmes-Farley et al. |
| 6,605,270 | B1 | 8/2003 | Mandeville et al. |
| 6,858,203 | B2 | 2/2005 | Holmes-Farley et al. |
| 7,014,846 | B2 | 3/2006 | Holmes-Farley et al. |
| 7,459,151 | B2 | 12/2008 | Holmes-Farley et al. |
| 7,638,524 | B2 | 12/2009 | Huval et al. |
| 2003/0133902 | A1 | 7/2003 | Holmes-Farley et al. |
| 2009/0226392 | A1 | 9/2009 | Holmes-Farley et al. |

FOREIGN PATENT DOCUMENTS

| | | | |
|---|---|---|---|
| DE | 4010271 | A1 | 10/1991 |
| EP | 0162388 | A1 | 11/1985 |
| EP | 0375350 | A2 | 6/1990 |
| EP | 0379161 | A2 | 7/1990 |
| EP | 0449151 | A2 | 10/1991 |
| EP | 0534304 | A1 | 3/1993 |
| EP | 0605757 | A1 | 7/1994 |
| EP | 0737759 | A1 | 10/1996 |
| EP | 0997148 | A1 | 5/2000 |
| EP | 1153940 | A1 | 11/2001 |
| EP | 1304104 | A2 | 4/2003 |
| FR | 2217010 | A1 | 9/1974 |
| FR | 2232563 | | 1/1975 |
| GB | 929391 | A | 6/1963 |
| GB | 1238597 | A | 7/1971 |
| GB | 2036948 | A | 7/1980 |
| GB | 1573487 | A | 8/1980 |
| GB | 2090605 | | 7/1982 |
| GB | 2276170 | A | 9/1994 |
| GB | 2391730 | A | 2/2004 |
| JP | 10330269 | A2 | 12/1998 |
| NL | 7401543 | | 8/1974 |
| NL | 7603653 | | 10/1976 |
| RU | 1808015 | A3 | 4/1993 |
| WO | 1990002148 | | 3/1990 |
| WO | 199210522 | A1 | 6/1992 |
| WO | 199300915 | | 1/1993 |
| WO | 199305793 | | 4/1993 |
| WO | 199404596 | | 3/1994 |
| WO | 199419379 | | 9/1994 |
| WO | 199427620 | A1 | 12/1994 |
| WO | 199427621 | A1 | 12/1994 |
| WO | 199505184 | A2 | 2/1995 |
| WO | 199621454 | A1 | 7/1996 |
| WO | 1996025440 | | 8/1996 |
| WO | 199749771 | A1 | 12/1997 |
| WO | 1999022721 | | 5/1999 |
| WO | 2000022008 | | 4/2000 |
| WO | 02085377 | A1 | 10/2002 |
| WO | 2005065291 | | 7/2005 |
| WO | 2006022759 | | 3/2006 |
| WO | 2006050314 | | 5/2006 |
| WO | 2011106542 | A2 | 9/2011 |
| WO | 2011106545 | A1 | 9/2011 |
| WO | 2011106548 | A1 | 9/2011 |
| WO | 2012027331 | A1 | 3/2012 |

OTHER PUBLICATIONS

International Search Report and Written Opinion for Application No. PCT/US2015/066006, dated Jun. 10, 2016, 52 pages.

Potthoff, et al., Colesevelam Suppresses Hepatic Glycogenolysis by TGR5-Mediated Induction of GLP-1 Action in DIO Mice, Am. J. Physiol. Gastrointest. Liver Physiol., vol. 304, pp. G371-G380, (2013).

Herrema, et al., Bile Salt Sequestration Induces Hepatic De Novo Lipogenesis Through Farnesoid X Receptor- and Liver X Receptor alpha-Controlled Metabolic Pathways in Mice, Hepatology, vol. 51, No. 3, (2010), 806-816.

Meissner, et al., Bile Acid Sequestration Reduces Plasma Glucose Levels in db/db Mice by Increasing Its Metabolic Clearance Rate, PLoS One, (2011), vol. 6, No. 11, pp. 1-8.

Sugimoto-Kawabata, et al., Colestilan Decreases Weight Gain by Enhanced NEFA Incorporation in Biliary Lipids and Fecal Lipid Excretion, Journal of Lipid Research, vol. 54, (2013), pp. 1255-1264.

Staels, et al., Bile Acids and Metabolic Regulation, Diabetes Care, vol. 32, Supplement 2, (2009), pp. S237-S245.

Mendonca, et al., Polymeric Bile Acid Sequestrants—Synthesis Using Conventional Methods and New Approaches Based on "Controlled"/Living Radical Polymerization, Prog Polym Sci, 38, (2013), pp. 445-461.

Prawitt, et al., Glucose-Lowering Effects of Intestinal Bile Acid Sequestration Through Enhancement of Splanchnic Glucose Utilization, Trends in Endocrinology and Metabolism, (2014), vol. 25, No. 5, pp. 235-244.

Holst, et al., Potential New Approaches to Modifying Intestinal GLP-1 Secretion in Patients With Type 2 Diabetes Mellitus, Clin Drug Investig, (2012), vol. 32, No. 1, pp. 1-14.

(56) References Cited

OTHER PUBLICATIONS

Braulin, et al., Bile Acid Binding to Sevelamer HC1, Kidney International, vol. 62, (2002), pp. 611-619.

Polomoscanik, et al., Hydrophobically Modified Poly(Allylamine) Hydrogels Containing Internal Quaternary Ammonium Groups as Cholesterol Lowering Agents: Synthesis, Characterization, and Biological Studies, Journal of Macromolecular Science, Part A: Pure and Applied Chemistry, (2012), vol. 49, pp. 1-11.

Huval, et al., Novel Cholesterol Lowering Polymeric Drugs Obtained by Molecular Imprinting, Macromolecules, (2001), vol. 34, pp. 1548-1550.

Huval, et al., Syntheses of Hydrophobically Modified Cationic Hydrogels by Copolymerization of Alkyl Substituted Diallylamine Monomers and Their Use as Bile Acid Sequestrants, European Polymer Journal, vol. 40, (2004), pp. 693-701.

Smushkin, et al., The Effect of a Bile Acid Sequestrant on Glucose Metabolism in Subjects With Type 2 Diabetes, Diabetes, (2013), vol. 62, No. 4, pp. 1094-1101.

Kondo, et al., Colestilan Monotherapy Significantly Improves Glycaemic Control and LDL Cholesterol Levels in Patients With Type 2 Diabetes: A Randomized Double-Blind Placebo-Controlled Study, Diabetes, Obesity and Metabolism, (2010), vol. 12, pp. 246-251.

Suzuki, et al., The Effects of Colestimide on Blood Glucose-Lowering Activity and Body Weight in Patients With Type 2 diabetes and Hypercholesterolemia, J Nippon Med Sch, (2007), vol. 74, No. 1, pp. 81-84.

Suzuki, et al., Effects of Bile-Acid-Binding Resin (Colestimide) on Blood Glucose and Visceral Fat in Japanese Patients With Type 2 Diabetes Mellitus and Hypercholesterolemia: An Open-Label, Randomized, Case-Control, Crossover Study, Journal of Diabetes and Its Complications, vol. 26, No. 1, pp. 34-39, (2012).

* cited by examiner

Figure 1: General Synthesis Scheme for Crosslinked Polydiallylamine-Polyvinlyamine (PDA-PVAm) Copolymers
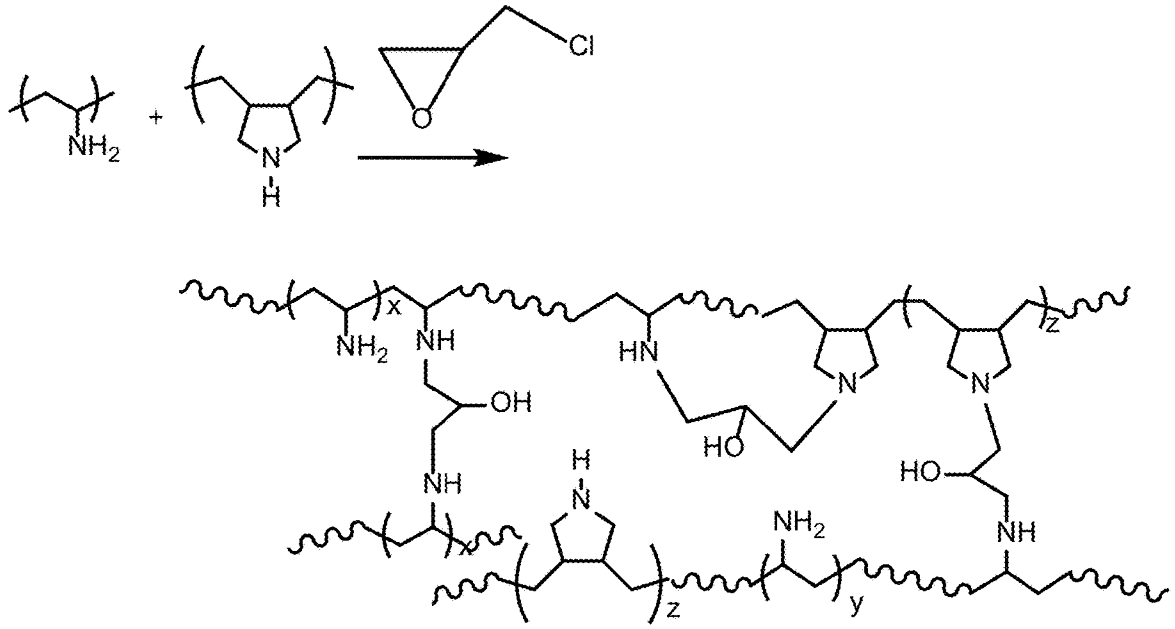

Figure 2: General Synthesis Scheme for Crosslinked Polydiallylamine-Polyallylamine (PDA-PAA) Copolymers
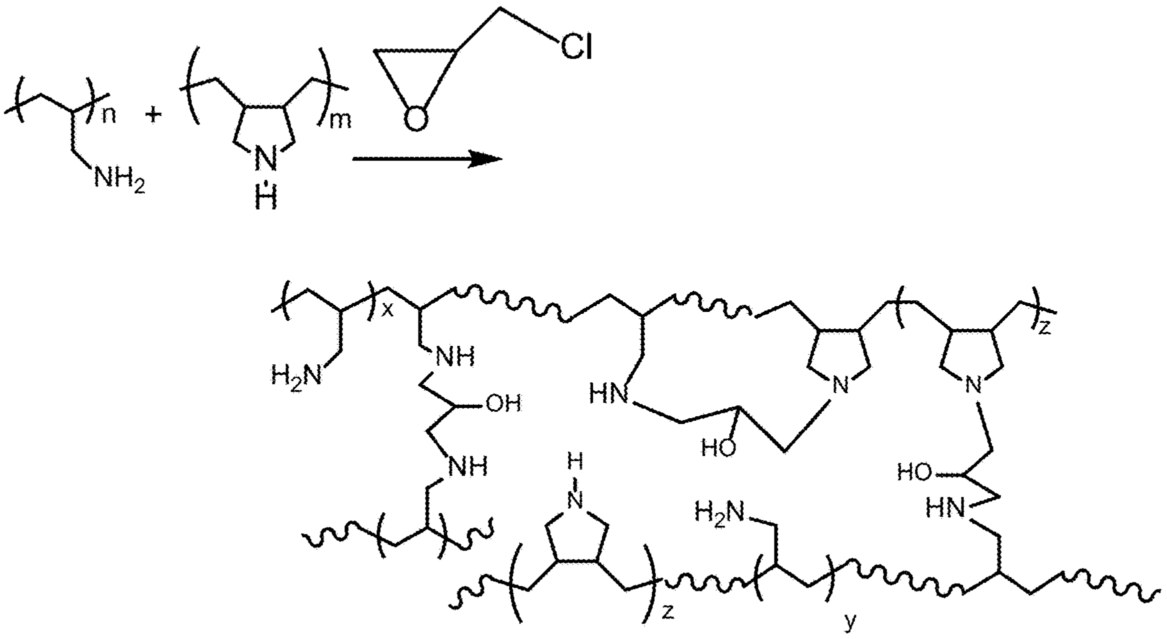

Figure 3: *In vivo* Effect on Blood Glucose with Crosslinked PDA-PVAm Copolymers after 4 Weeks of Treatment
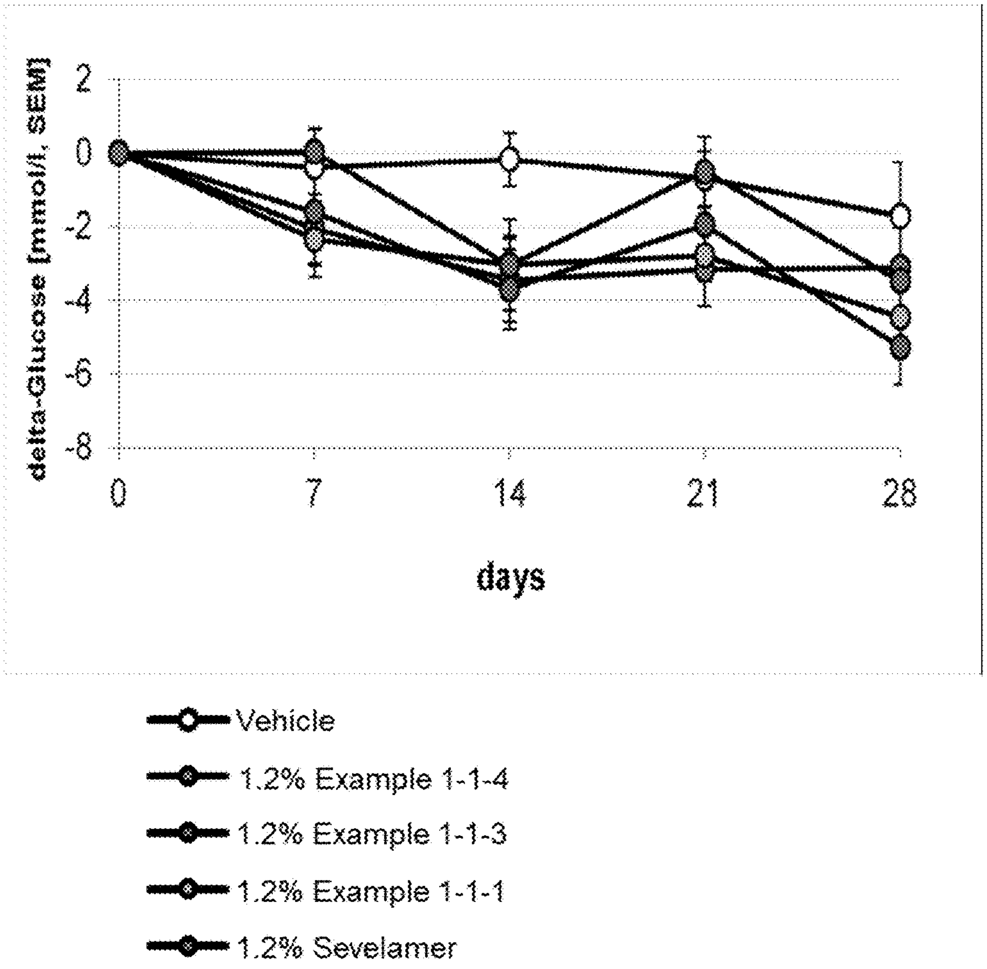

**Figure 4: *In vivo* Effect on $HbA_{1C}$ with Crosslinked PDA-PVAm Copolymers after 4 Weeks of Treatment**
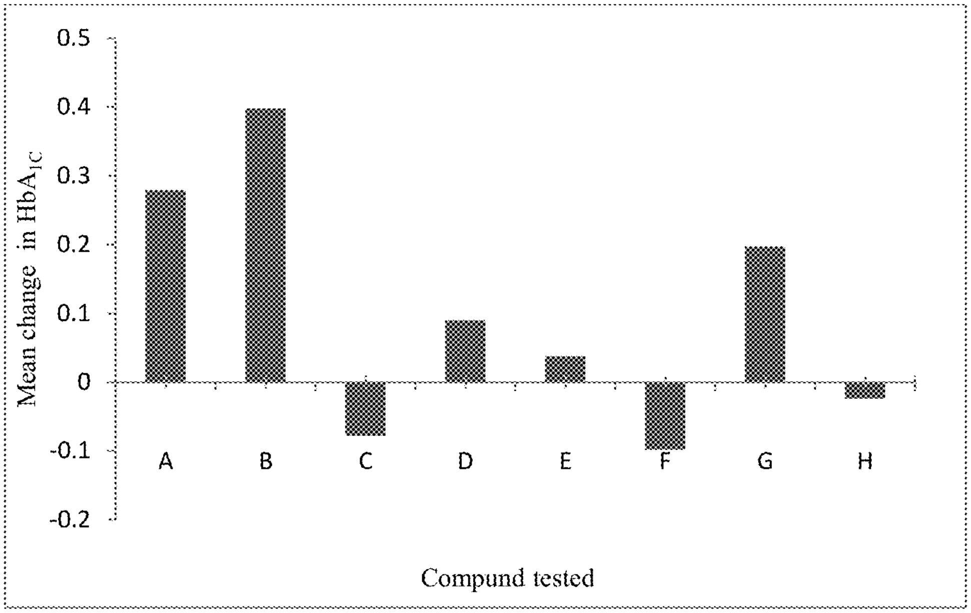
A = vehicle control; B = sevelamer; C = linagliptin; D = Example 1- 1- 4; E = Example 1- 1- 3; F = Example 1- 1- 1; G = sevelamer + linagliptin; H = Example 1 1- 3 + linagliptin Figure 5: *In vivo* Effect on Blood Glucose with Crosslinked PDA-PAA Copolymers
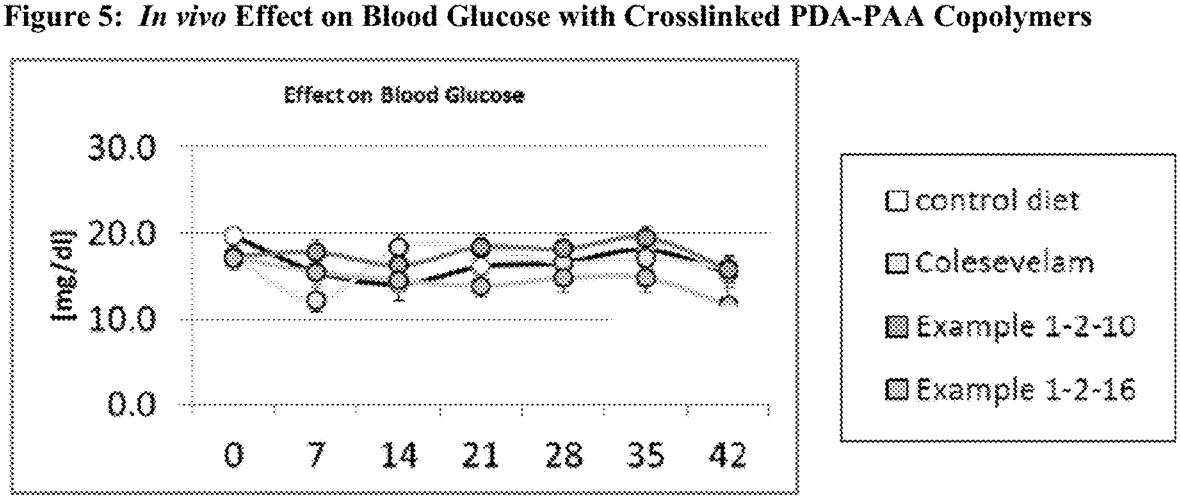

Figure 6: *In vivo* Effect on HbA1c with Crosslinked PDA-PAA Copolymers
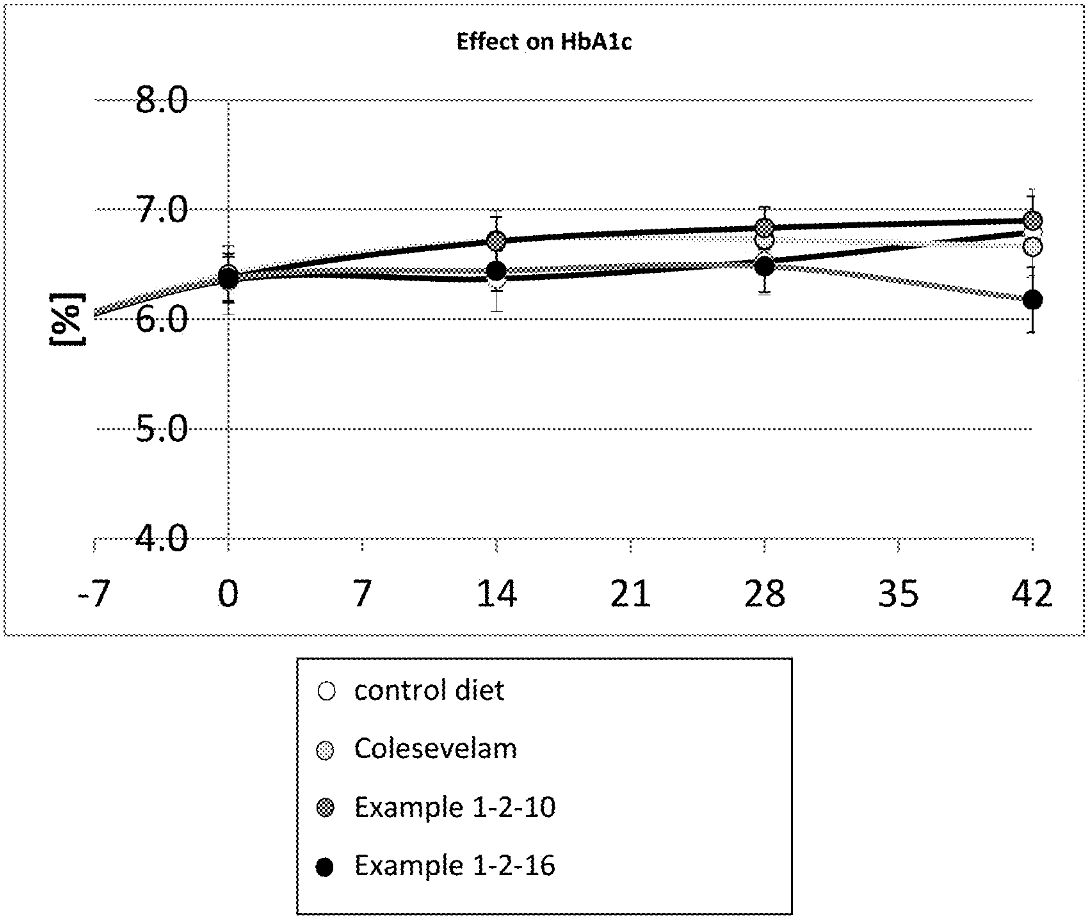

Figure 7: *In vivo* Effect on Liver Weight with Crosslinked PDA-PAA Copolymers
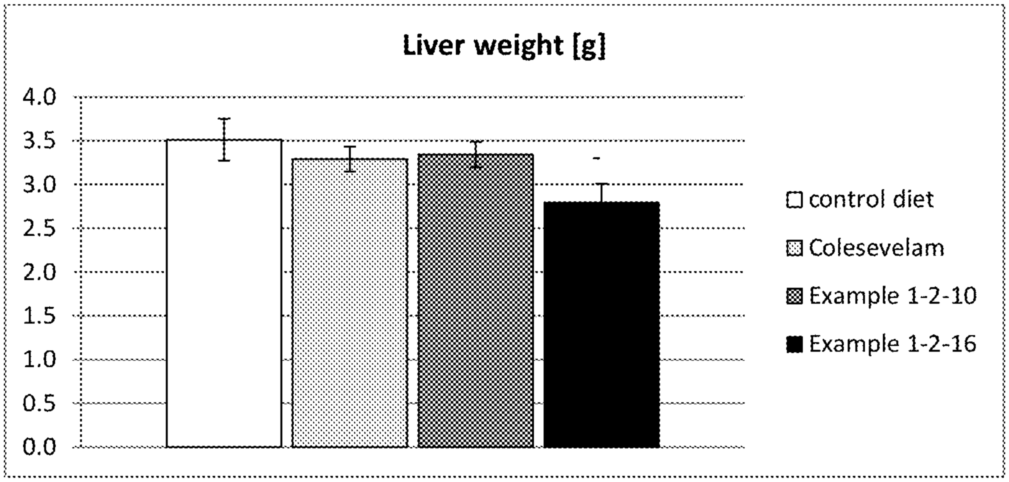

Figure 8: *In vivo* Effect on Liver Triglycerides with Crosslinked PDA-PAA Copolymers
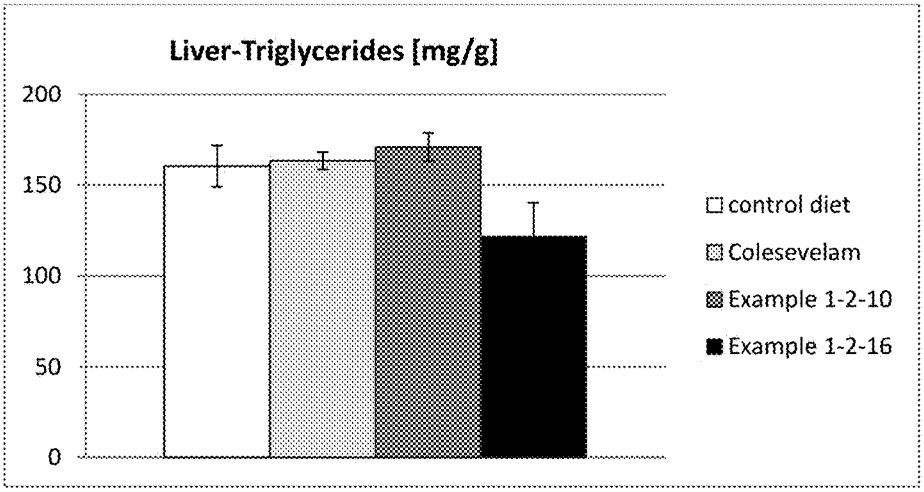

Figure 9: *In vivo* Effect on Blood Glucose Profile with Crosslinked PDA-PVAm and PDA-PAA Copolymers
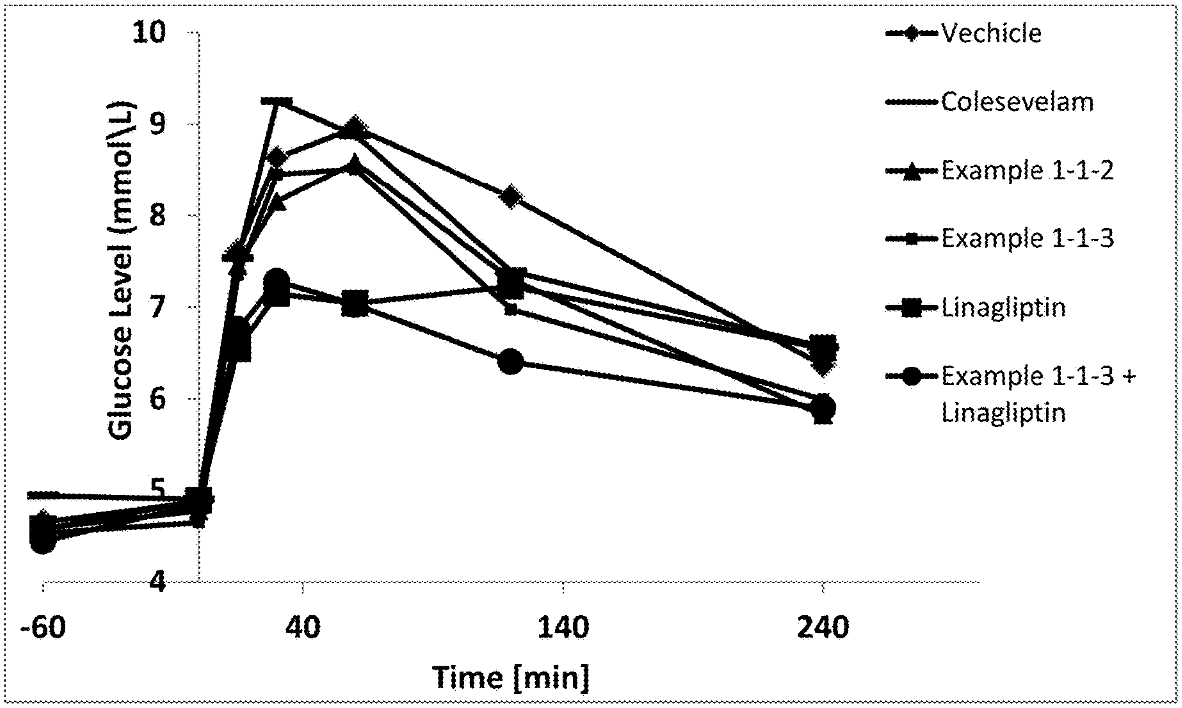

Figure 10: *In vivo* Effect on Blood Glucose of KKAy mice treated with Crosslinked PDA-PAA Copolymer after 7 Weeks of Treatment
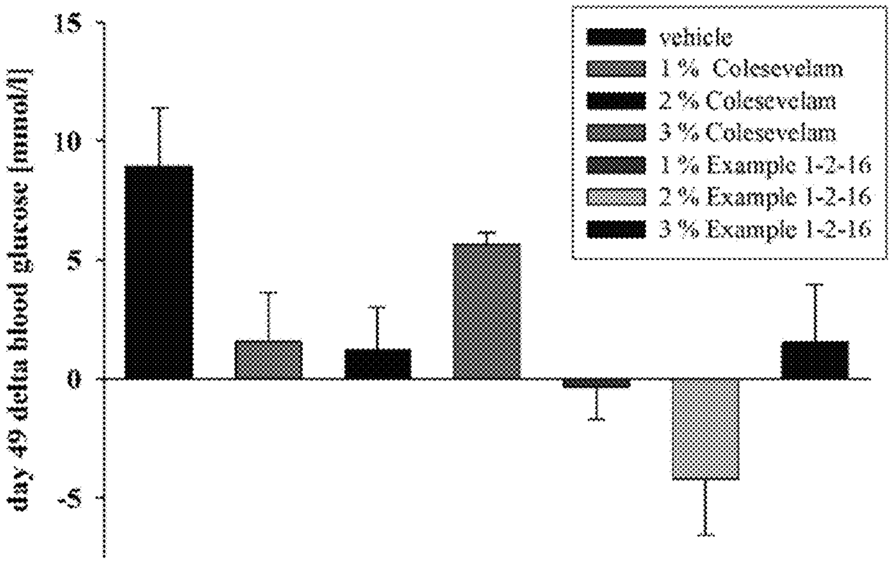

Figure 11: *In vivo* Effect on HbA1c of KKAy mice treated with Crosslinked PDA-PAA Copolymer after 7 Weeks of Treatment
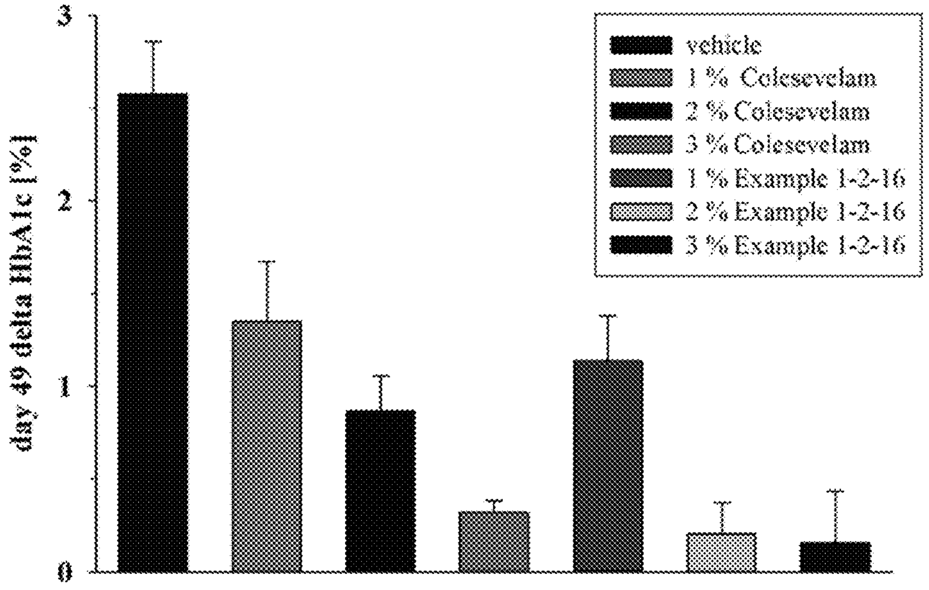

CROSSLINKED POLYDIALLYMINE COPOLYMERS FOR THE TREATMENT OF TYPE 2 DIABETES

CROSS-REFERENCE TO RELATED APPLICATIONS

This application claims the benefit of priority to U.S. Provisional Application No. 62/093,751 filed Dec. 18, 2014, the disclosure of which is incorporated herein in its entirety.

BACKGROUND OF THE INVENTION

1. Field of the Invention

This invention relates to polydiallymine copolymers for the treatment of diabetes. The polydiallylamine copolymers of the instant invention consist of polydiallymine monomers and polyallylamine or polyvinylamine monomers. This invention further relates to the use of polydiallymine copolymers as pharmaceutical agents and in pharmaceutical compositions.

Type 2 diabetes is a chronic disease marked by elevated blood sugar levels; it manifests in individuals whose body produces insufficient amounts of insulin or becomes resistant to insulin. The primary causes of type 2 diabetes are physical inactivity and overweight/obesity. According to the Centers for Disease Control and Prevention's *National Diabetes Statistics Report* (2014), approximately 29.1 million Americans, 9.3% of the total population, have diabetes. The World Health Organization estimates that approximately 347 million people worldwide have diabetes, with 90% of those people suffering from type 2 diabetes.

Subjects with type 2 diabetes often suffer from comorbid conditions in addition to their type 2 diabestes. Comorbid conditions include but are not limited to cardiovascular diseases including hypertension and dyslipidemia, non-alcoholic fatty liver disease, decreased renal function including but not limited to chronic kidney disease (CKD), depression and osteoarthritis.

DEFINITIONS

As used herein, the term "amino" means a functional group having a nitrogen atom and 1 to 2 hydrogen atoms. "Amino" generally may be used herein to describe a primary, secondary, or tertiary amine, and those of skill in the art will readily be able to ascertain the identification of which in view of the context in which this term is used in the present disclosure. The term "amine" or "amine group" or "ammonia group" means a functional group containing a nitrogen atom derived from ammonia ($NH_3$). The amine groups may be primary amines, meaning the nitrogen is bonded to two hydrogen atoms and one substituent group comprising a substituted or unsubstituted alkyl or aryl group or an aliphatic or aromatic group. The amine groups may be secondary amines meaning, the nitrogen is bonded to one hydrogen atom and two substituent groups comprising a substituted or unsubstituted aklyl or aryl groups or an aliphatic or aromatic group, as defined below. The amine groups may be tertiary amines meaning the nitrogen is bonded to three substituent groups comprising a substituted or unsubstituted aklyl or aryl groups or an aliphatic or aromatic group. The amine groups may also be quaternary amines meaning the designated amine group is bonded to a fourth group, resulting in a positively charged ammonium group.

As used herein, the term "amide group" means a functional group comprising a carbonyl group linked to a nitrogen. A "carbonyl group" means a functional group comprising a carbon atom double bonded to an oxygen atom, represented by (C═O).

The term "alkane" means a saturated hydrocarbon, bonded by single bonds. Alkanes can be linear or branched. "Cycloalkanes" are saturated hydrocarbons rings bonded by single bonds.

As used herein, the term "($C_1$-$C_{10}$)alkyl" means a saturated straight chained or branched or cyclic hydrocarbon consisting essentially of 1 to 10 carbon atoms and a corresponding number of hydrogen atoms. Typically straight chained or branched groups have from one to ten carbons, or more typically one to five carbons. Exemplary ($C_1$-$C_{10}$)alkyl groups include methyl (represented by $—CH_3$), ethyl (represented by $—CH_2$-$CH_3$), n-propyl, isopropyl, n-butyl, isobutyl, etc. Other ($C_1$-$C_{10}$)alkyl groups will be readily apparent to those of skill in the art given the benefit of the present disclosure.

As used herein, the term "($C_2$-$C_9$)heteroalkyl" means a saturated straight chained or branched or cyclic hydrocarbon consisting essentially of 2 to 10 atoms, wherein 2 to 9 of the atoms are carbon and the remaining atom(s) is selected from the group consisting of nitrogen, sulfur, and oxygen. Exemplary ($C_2$-$C_9$)heteroalkyl groups will be readily apparent to those of skill in the art given the benefit of the present disclosure.

As used herein, the term "($C_3$-$C_{10}$)cycloalkyl" means a nonaromatic saturated hydrocarbon group, forming at least one ring consisting essential of 3 to 10 carbon atoms and a corresponding number of hydrogen atoms. ($C_3$-$C_{10}$)cycloalkyl groups can be monocyclic or multicyclic. Individual rings of multicyclic cycloalkyl groups can have different connectivities, for example, fused, bridged, spiro, etc., in addition to covalent bond substitution. Exemplary ($C_3$-$C_{10}$) cycloalkyl groups include cyclopropyl, cyclobutyl, cyclopentyl, cyclohexyl, norbornanyl, bicyclo-octanyl, octahydro-pentalenyl, spiro-decanyl, cyclopropyl substituted with cyclobutyl, cyclobutyl substituted with cyclopentyl, cyclohexyl substituted with cyclopropyl, etc. Other ($C_3$-$C_{10}$) cycloalkyl groups will be readily apparent to those of skill in the art given the benefit of the present disclosure.

As used herein, the term "($C_2$-$C_9$)heterocycloalkyl" means a nonaromatic group having 3 to 10 atoms that form at least one ring, wherein 2 to 9 of the ring atoms are carbon and the remaining ring atom(s) is selected from the group consisting of nitrogen, sulfur, and oxygen. ($C_2$-$C_9$)heterocycloalkyl groups can be monocyclic or multicyclic. Individual rings of such multicyclic heterocycloalkyl groups can have different connectivities, for example, fused, bridged, spiro, etc., in addition to covalent bond substitution. Exemplary ($C_2$-$C_9$)heterocycloalkyl groups include pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo

[4.1.0]heptanyl, 3-azabicyclo[3.1.0]hexanyl, 2-azaspiro[4.4]nonanyl, 7-oxa-1-aza-spiro[4.4]nonanyl, 7-azabicyclo[2.2.2]heptanyl, octahydro-1H-indolyl, etc. The ($C_2$-$C_9$) heterocycloalkyl group is typically attached to the main structure via a carbon atom or a nitrogen atom. Other ($C_2$-$C_9$)heterocycloalkyl groups will be readily apparent to those of skill in the art given the benefit of the present disclosure.

The term "aliphatic group" or "aliphatic" means a non-aromatic group consisting of carbon and hydrogen, and may optionally include one or more double and/or triple bonds. An aliphatic group may be straight chained, branched or cyclic and typically contains between about one and about 24 carbon atoms.

The term "aryl group" may be used interchangeably with "aryl," "aryl ring," "aromatic," "aromatic group," and "aromatic ring." Aryl groups include carbocyclic aromatic groups, typically with six to fourteen ring carbon atoms. Aryl groups also include heteroaryl groups, which typically have five to fourteen ring atoms with one or more heteroatoms selected from nitrogen, oxygen and sulfur.

As used herein, the term "($C_6$-$C_{14}$)aryl" means an aromatic functional group having 6 to 14 carbon atoms that form at least one ring.

As used herein, the term "($C_2$-$C_9$)heteroaryl" means an aromatic functional group having 5 to 10 atoms that form at least one ring, wherein 2 to 9 of the ring atoms are carbon and the remaining ring atom(s) is selected from the group consisting of nitrogen, sulfur, and oxygen. ($C_2$-$C_9$)heteroaryl groups can be monocyclic or multicyclic. Individual rings of such multicyclic heteroaryl groups can have different connectivities, for example, fused, etc., in addition to covalent bond substitution. Exemplary ($C_2$-$C_9$)heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. The ($C_2$-$C_9$)heteroaryl group is typically attached to the main structure via a carbon atom, however, those of skill in the art will realize when certain other atoms, for example, hetero ring atoms, can be attached to the main structure. Other ($C_2$-$C_9$)heteroaryl groups will be readily apparent to those of skill in the art given the benefit of the present disclosure.

As used herein, the term "alkyl amine" means an ($C_1$-$C_{10}$)alkyl containing a primary, secondary, or tertiary amine group in place of one hydrogen atom, represented by ($C_1$-$C_{10}$)alkyl amine and (($C_1$-$C_{10}$)alkyl)$_2$ amine.

The term "alkyl ester" means a ($C_1$-$C_{10}$)alkyl containing an ester group in place of one hydrogen atom, represented by —O(O)C—($C_1$-$C_{10}$)alkyl.

The term "alkyl acid" means an ($C_1$-$C_{10}$)alkyl containing a carboxylic acid group in place of one hydrogen atom, represented by ($C_1$-$C_{10}$)alkyl-COOH.

The term "aliphatic acid" means an acid of nonaromatic hydrocarbons, represented by ($C_3$-$C_{10}$)cycloalkyl-COOH.

The term "halo" means a fluorine (F), chlorine (Cl), bromine (Br), iodine (I), or astatine (At) ion.

The term "methoxy" means a ($C_1$)alkyl containing an oxygen in place of one hydrogen atom, represented by —(O)$CH_3$.

The term "polyol" means an alcohol containing multiple hydroxyl (—OH) groups.

"Substituted" means the substitution of a carbon in alkyl, heterocyclic or aryl groups with one or more non-carbon substituent. Non-carbon substituents are selected from nitrogen, oxygen and sulfur.

"Unsubstituted" means the group is comprised of only hydrogen and carbon.

The term "polymer" means a molecule comprised of repeating units. The term "repeat unit" or "monomer" means a group in a polymer that repeats or appears multiple times in a polymer. A polymer may be a copolymer if the repeating units or "comonomers" are chemically and structurally different from one another.

The term "polymer chain" is a network of repeat units that comprise a polymer. A polymer may comprise a single polymer chain or multiple polymer chains.

The disclosed polymers are typically crosslinked with multifunctional crosslinking groups. The term "crosslinked" means a bond connecting one polymer chain to another polymer chain or a bond internally connecting a single polymer chain. The term "internally cross-linked" means a polymer chain with a bond connecting different points on a single polymer chain. The term "multifunctional crosslinking group" means a group which connects two or more repeat units or polymerized monomers within a polymer. Multifunctional crosslinking groups in the disclosed polymers are typically covalently bonded to the nitrogen atoms in the polymerized amine monomers or amine repeat units. In one option, the disclosed polymer comprises only one type of crosslinking group. Alternatively, the disclosed polymer comprises two or more different crosslinking groups.

Multifunctional crosslinking groups in the disclosed polymers are typically formed from multifunctional crosslinking agents, which comprise two or more electrophilic groups capable of reacting and forming a covalent bond with a nitrogen atom. Examples of suitable electrophilic groups include halide, epoxide, acrylate, arylsulfonate and alkylsulfonate. Reaction of a multifunctional crosslinking agent with an amine monomer disclosed herein can form a disclosed polymer. The portion of a multifunctional crosslinking agent remaining after it reacts with the amine monomer forms a crosslinking group and is also referred to as the "residue of the crosslinking agent". For example, $—(CH_2)_6—$ is the crosslinking group formed from the crosslinking agent 1,6-dibromohexane and is also the residue of 1,6-dibromohexane.

Examples of suitable types crosslinking agents include dihaloalkane, haloalkyloxirane, alkyloxirane sulfonate, di(haloalkyl)amine, tri(haloalkyl)amine, diepoxide, triepoxide, tetraepoxide, bis(halomethyl) benzene, tri(halomethyl) benzene) and tetra(halomethyl) benzene.

Specific examples of crosslinking agents include epichlorohydrin, epibromohydrin, (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol digylcidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy) diphenylmethane, bisphenol F diglycidyl ether, 1,4-bis(2',3'-epoxypropyl)perfluoro-n-butane, 2, 6-di(oxiran-2-ylmethyl)-1,2,3,5,6,7-hexahydropyrrolo[3,4-f]isoindol-1,3,5,7-tetraone, bisphenol A diglycidyl ether, ethyl 5-hydroxy-6,8-di(oxiran-2-ylmethyl)-4-oxo-4h-chromene-2-carboxylate, bis[4-(2,3-epoxy-propylthio)phenyl]-sulfide, 1,3-bis(3-glycidoxypropyl)tetramethyldisiloxane, 9,9-bis[4-(glycidyloxy)phenyl]fluorene, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris [[3-(epoxypropoxy)propyl]dimethylsilyloxy]-1,3,5,7,9,11,14-heptacyclopentyltricyclo[7.3.3.15,11]heptasiloxane, 4,4'-methylenebis(N,N-diglycidylaniline), bis(halomethyl) benzene, bis(halomethyl)biphenyl and bis(halomethyl) naphthalene.

The term "pharmaceutically acceptable anion" means an anion that is suitable for pharmaceutical use. Pharmaceutically acceptable anions include but are not limited to halides, carbonate, bicarbonate, sulfate, bisulfate, hydroxide, nitrate, persulfate, sulfite, acetate, ascorbate, benzoate, citrate, dihydrogen citrate, hydrogen citrate, oxalate, succinate, tartrate, taurocholate, glycocholate, and cholate.

A "guanidino group" is represented by Formula (A):

(A)

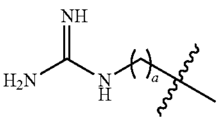

wherein a is an integer from 0 to 25,

A "guanidinium chloride group" is represented by Formula (B), (B)

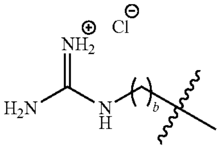

wherein b is an integer from 0 to 25,

A "guanidinobenzene group" is represented by Formula (C), (C)

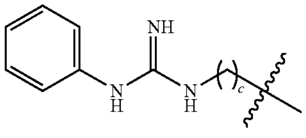

wherein c is an integer from 0 to 25,

A "dihydroxy group" is represented by Formula (D), (D)

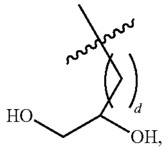

wherein d is an integer from 0 to 25,

A "polyethylene glycol group" is represented by Formula (E)

(E)

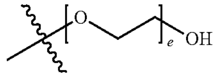

wherein e is an integer from 1 to 400.

The term "effective amount" of a disclosed amine functional polyamides is a quantity sufficient to achieve a therapeutic and/or prophylactic effect on the particular condition being treated, such as an amount which results in the prevention or a decrease in the symptoms associated with mucositis, oral mucositis, infection and surgical site infection, and lung infection associated with cystic fibrosis. The precise amount of the disclosed amine functional polyamides that is administered will depend on the type and severity of mucositis or infection being treated and on the characteristics of the individual, such as general health, age, sex, body weight and tolerance to drugs.

2. Related Art

Not applicable

BRIEF SUMMARY OF THE INVENTION

In a first embodiment, the invention relates to a polydiallyamine copolymer comprising a polymer chain according to Formula (I):

$$A - [(B)_u (C)_v]_w - D \qquad (I)$$

wherein:

u, and v are each independently an integer from 0 to 200,000; and w is an integer from 1 to 200,000;

A, B, C and D are each independently repeat units selected from Formula (II) or Formula (III);

wherein Formula (II) is according to the structural formula:

(II)

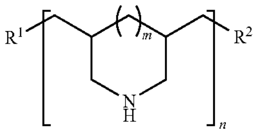

or a pharmaceutically acceptable salt thereof, wherein:
- m is 0 or 1;
- n is an integer from 1 to 200,000;
- $R^1$ and $R^2$ are each independently a pharmaceutically acceptable end group or a point of attachment to another repeat unit of the copolymer;

and Formula (III) is according to the structural formula:

(III)

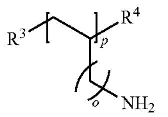

or a pharmaceutically acceptable salt thereof, wherein:
- o is 0 or 1;
- p is an integer from 1 to 200,000;
- $R^3$ and $R^4$ are each independently a pharmaceutically acceptable end group or a point of attachment to another repeat unit of the copolymer;

with the proviso that the copolymer of Formula (I) is not exclusively a polymer of Formula (II) or exclusively a polymer of Formula (III).

In a second embodiment, the invention relates to a polydiallylamine copolymer comprising two or more polymer chains, wherein each polymer chain is according to Formula (I):

$$A - [(B)_u (C)_v]_w - D \quad (I)$$

wherein:
- u, and v are each independently an integer from 0 to 200,000; and
- w is an integer from 1 to 200,000,
- A, B, C and D are each independently repeat units selected from Formula (II) or Formula (III);
- wherein Formula (II) is according to the structural formula:

(II)

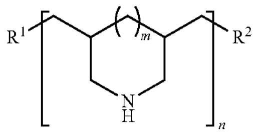

or a pharmaceutically acceptable salt thereof, wherein:
- m is 0 or 1;
- n is an integer from 1 to 200,000;
- $R^1$ and $R^2$ are each independently a pharmaceutically acceptable end group or a point of attachment to another repeat unit of the copolymer;

and Formula (III) is according to the structural formula:

(III)

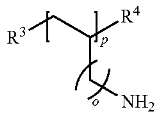

or a pharmaceutically acceptable salt thereof, wherein:
- o is 0 or 1;
- p is an integer from 1 to 200,000;
- $R^3$ and $R^4$ are each independently a pharmaceutically acceptable end group or a point of attachment to another repeat unit of the copolymer;

and wherein:
- (a) each polymer chain must be cross-linked with at least one other polymer chain, and
- (b) each polymer chain may be internally cross-linked.

In a third embodiment, the invention relates to a pharmaceutical composition comprising a polydiallyamine copolymer comprising a polymer chain according to Formula (I):

$$A - [(B)_u (C)_v]_w - D \quad (I)$$

wherein:
- u, and v are each independently an integer from 0 to 200,000; and
- w is an integer from 1 to 200,000;
- A, B, C and D are each independently repeat units selected from Formula (II) or Formula (III);
- wherein Formula (II) is according to the structural formula:

(II)

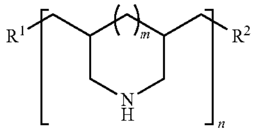

or a pharmaceutically acceptable salt thereof, wherein:
- m is 0 or 1;
- n is an integer from 1 to 200,000;
- $R^1$ and $R^2$ are each independently a pharmaceutically acceptable end group or a point of attachment to another repeat unit of the copolymer;

and Formula (III) is according to the structural formula:

(III)

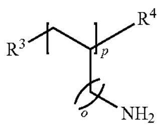

or a pharmaceutically acceptable salt thereof, wherein:
- o is 0 or 1;
- p is an integer from 1 to 200,000;
- $R^3$ and $R^4$ are each independently a pharmaceutically acceptable end group or a point of attachment to another repeat unit of the copolymer;

with the proviso that the copolymer of Formula (I) is not exclusively a polymer of Formula (II) or exclusively a polymer of Formula (III).

In a fourth embodiment, the invention relates to a pharmaceutical composition comprising a polydiallyamine copolymer comprising two or more polymer chains, wherein each polymer chain is according to Formula (I):

(I)

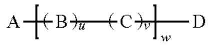

wherein:

u, and v are each independently an integer from 0 to 200,000; and w is an integer from 1 to 200,000, A, B, C and D are each independently repeat units selected from Formula (II) or Formula (III);

wherein Formula (II) is according to the structural formula:

(II)

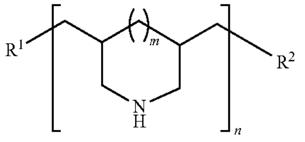

or a pharmaceutically acceptable salt thereof, wherein:

m is 0 or 1;

n is an integer from 1 to 200,000;

$R^1$ and $R^2$ are each independently a pharmaceutically acceptable end group or a point of attachment to another repeat unit of the copolymer;

and Formula (III) is according to the structural formula:

(III)

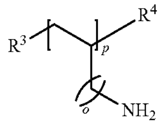

or a pharmaceutically acceptable salt thereof, wherein:

o is 0 or 1;

p is an integer from 1 to 200,000;

$R^3$ and $R^4$ are each independently a pharmaceutically acceptable end group or a point of attachment to another repeat unit of the copolymer;

and wherein:

(a) each polymer chain must be cross-linked with at least one other polymer chain, and (b) each polymer chain may be internally cross-linked.

In a fifth embodiment, the invention relates to methods of using the polydiallylamine copolymers and pharmaceutical compositions comprising polydiallylamine copolymers. These methods relate to the administration of the polydiallylamine copolymers and pharmaceutical compositions comprising polydiallylamine copolymers for the treatment of type 2 diabetes, the mitigation of complications associated with type 2 diabetes, the reduction of blood hemoglobin, the improvement of insulin resistance, the improvement of lipid profile, the reduction of LDL cholesterol, the reduction of total cholesterol, the lowering of elevated lipids, the binding of dietary lipids, the lowering of uremic toxins, the reduction of serum phosphorous, the reduction of absorption of dietary phosphate, the binding AGE precursors, the binding of dietary, the reduction of oxidative stress, the binding of bile acids and the reduction of body fat, to a subject in need thereof.

BRIEF DESCRIPTION OF THE SEVERAL VIEWS OF THE DRAWING(S)

FIG. 1. General Synthesis Scheme for Crosslinked Polydiallylamine-Polyvinlyamine (PDA-PVAm) Copolymers. The starting monomers polydiallylamine and polyvinlyamine are reacted with crosslinking agent under various conditions to yield the resulting PDA-PVAm copolymers described in the examples.

FIG. 2. General Synthesis Scheme for Crosslinked Polydiallylamine-Polyallylamine (PDA-PAA) Copolymers. The starting monomers polydiallylamine and polyallylamine are reacted with crosslinking agent under various conditions to yield the resulting PDA-PAA copolymers described in the examples.

FIG. 3. In vivo Effect on Blood Glucose with Crosslinked PDA-PVAm Copolymers after 4 Weeks of Treatment. The in vivo effect on blood glucose in ten week old male lean (C57BL/6J) and obese, diabetic db/db mice (C57BL6/J) were measured for animals treated with control vehicle, PDA-PVAm (12.5:87.5 mole/mole) copolymer, PDA-PVAm (50:50 mole/mole) copolymer, PDA-PVAm (75:25 mole/mole) copolymer, sevelamer and linagliptin at days 0, 7, 14 and 28 post-treatment are presented.

FIG. 4. In vivo Effect on $HbA_{1C}$ with Crosslinked PDA-PVAm Copolymers after 4 Weeks of Treatment. The in vivo effect on $HbA_{1C}$ in ten week old male lean (C57BL/6J) and obese, diabetic db/db mice (C57BL6/J) were measured for animals treated with control vehicle, PDA-PVAm (12.5:87.5 mole/mole) copolymer, PDA-PVAm (50:50 mole/mole) copolymer, PDA-PVAm (75:25 mole/mole) copolymer, sevelamer, linagliptin, sevelamer plus linagliptin, and PDA-PVAm (50:50 mole/mole) copolymer plus lingaliptin at 4 weeks post-treatment are presented.

FIG. 5. In vivo Effect on Blood Glucose Profile with Crosslinked PDA-PVAm Copolymers. The in vivo effect on blood glucose in Male Sprague Dawley rats of seven weeks age was evaluated by an oral glucose tolerance test (OGTT) using diet induced obese (DIO) rats as the disease models in rats treated with control vehicle, PDA-PVAm (25:75 mole/mole) copolymer, PDA-PVAm (50:50 mole/mole) copolymer, PDA-PVAm (50:50 mole/mole) copolymer plus linagaliptin, sevelamer, linagliptin, sevelamer plus linagliptin, and PDA-PVAm (50:50 mole/mole) copolymer plus lingaliiptin, colesevelam and lingaliptin at 40, 140 and 240 minutes post-treatment are presented.

FIG. 6. In vivo Effect on HbA1c with Crosslinked PDA-PAA Copolymers. The in vivo effects of different compositions of crosslinked PDA-PAA copolymers on blood HBA1C of dbd/db mice with escalating dose of test articles were measured. The animals were given increased dose of the compounds at two-week intervals (1 wt. % (day 0), 2 wt. % (day 14) and 3 wt. % (day 28) of diet).

FIG. 7. In vivo Effect on Liver Weight with Crosslinked PDA-PAA Copolymers. The in vivo effect of different compositions of crosslinked PDA-PAA copolymers on liver weight of dbd/db mice with escalating dose of test articles were measured. The animals were given increased dose of the compounds at two-week intervals (1 wt. % (day 0), 2 wt. % (day 14) and 3 wt. % (day 28) of diet).

FIG. 8. In vivo Effect on Liver Triglycerides with Crosslinked PDA-PAA Copolymers. The in vivo effect of different compositions of crosslinked PDA-PAA copolymers on liver triglyceride contents of dbd/db mice with escalating dose of test articles were measured. The animals were given increased dose of the compounds at two-week intervals (1 wt. % (day 0), 2 wt. % (day 14) and 3 wt. % (day 28) of diet).

FIG. 9. In vivo Effect on Blood Glucose Profile with Crosslinked PDA-PVAm and PDA-PAA Copolymers. The effect of polydiallylamine copolymers on improving insulin resistance (glucose homeostasis) was evaluated by an oral glucose tolerance test (OGTT) using diet induced obese (DIO) rats as the disease models.

FIG. 10. In vivo Effect on Blood Glucose of KKAy mice treated with Crosslinked PDA-PAA Copolymer after 7 Weeks of Treatment. The effect of treatment on blood glucose in diabetic KKAy mice was measured and the results are summarized as difference in their values at the start of the study and at the end of seven weeks of treatment.

FIG. 11. In vivo Effect on HbA1c of KKAy mice treated with Crosslinked PDA-PAA Copolymer after 7 Weeks of Treatment. The effect of treatment on HbA1c in diabetic KKAy mice was measured and the results are summarized as difference in their values at the start of the study and at the end of seven weeks of treatment.

DETAILED DESCRIPTION OF THE INVENTION

This invention relates to polydiallyamine copolymers. The polydiallyamine copolymers comprise monomers of polydiallylamine and monomers of polyallylamine or polyvinalyamine. The polydiallylaimine copolymers of the instant invention are crosslinked. Further, the polydiallylamine copolymers of the present invention are of varying molecular weights and are crosslinked to varying degrees. The polydiallylamine copolymers of the instant inventions offer certain advantages over other therapeutic polymers intended for similar uses.

The polydiallymine copolymers of the instant invention comprise a polymer chain according to Formula (I):

(I)

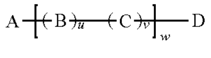

wherein:

- u, and v are each independently an integer from 0 to 200,000; and
- w is an integer from 1 to 200,000,
- A, B, C and D are each independently repeat units selected from Formula (II) or Formula (III);
  - wherein Formula (II) is according to the structural formula:

(II)

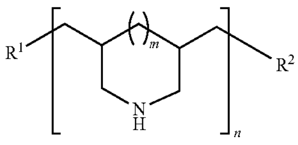

or a pharmaceutically acceptable salt thereof, wherein:

- m is 0 or 1;
- n is an integer from 1 to 200,000;
- $R^1$ and $R^2$ are each independently a pharmaceutically acceptable end group or a point of attachment to another repeat unit of the copolymer;

and Formula (III) is according to the structural formula:

(III)

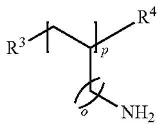

or a pharmaceutically acceptable salt thereof, wherein:

- o is 0 or 1;
- p is an integer from 1 to 200,000;
- $R^3$ and $R^4$ are each independently a pharmaceutically acceptable end group or a point of attachment to another repeat unit of the copolymer;

with the provisio that the copolymer of Formula (I) is not exclusively a polymer of Formula (II) or exclusively a polymer of Formula (III).

The polydiallylamine copolymers of the instant invention also comprise a copolymer comprising two to two million polymer chains, wherein each polymer chain is according to Formula (I):

(I)

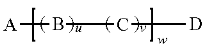

wherein:

- u, and v are each independently an integer from 0 to 200,000; and
- w is an integer from 1 to 200,000,
- A, B, C and D are each independently repeat units selected from Formula (II) or Formula (III);
  - wherein Formula (II) is according to the structural formula:

(II)

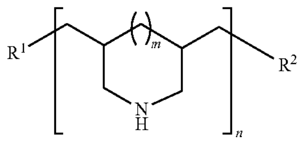

or a pharmaceutically acceptable salt thereof, wherein:

- m is 0 or 1;
- n is an integer from 1 to 200,000;
- $R^1$ and $R^2$ are each independently a pharmaceutically acceptable end group or a point of attachment to another repeat unit of the copolymer;

and Formula (III) is according to the structural formula:

(III)

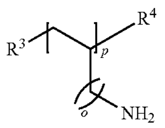

or a pharmaceutically acceptable salt thereof, wherein:

o is 0 or 1;

p is an integer from 1 to 200,000;

$R^3$ and $R^4$ are each independently a pharmaceutically acceptable end group or a point of attachment to another repeat unit of the copolymer;

and wherein:

(c) each polymer chain must be cross-linked with at least one other polymer chain, and (d) each polymer chain may be internally cross-linked.

The polydiallylamine copolymers of the instant invention are copolymers comprising monomers of Formula (II) and Formula (III) where m is 0. Alternatively, the polydiallylamine copolymers are copolymers comprising monomers of Formula (II) and Formula (III) where m is 1.

The polydiallylamine copolymers of the invention are copolymers comprising monomers of Formula (II) and Formula (III) where o is 0. In other cases, the polydiallylamine copolymers are copolymers comprising monomers of Formula (II) and Formula (III) where o is 1.

The polydiallylamine copolymers are copolymers comprising monomers of Formula (II) and Formula (III) where m is 0 and o is 0. In another preferred embodiment, the polydiallylamine copolymers are copolymers comprising monomers of Formula (II) and Formula (III) where m is 0 and o is 1.

The polydiallylamine copolymers are copolymers comprising monomers of Formula (II) and Formula (III) where m is 1 and o is 0. The polydiallylamine copolymers of the instant invention are copolymers comprising monomers of Formula (II) and Formula (III) where m is 1 and o is 1.

The polydiallylamine copolymers of the instant invention are terminated ($R^1$ and $R^2$, and $R^3$ and $R^4$) with pharmaceutically acceptable end groups. Representative examples of pharmaceutically acceptable end groups include, but are not limited to:

H, a group selected from $(C_1\text{-}C_{10})$alkyl, $(C_2\text{-}C_9)$heteroalkyl, $(C_3\text{-}C_{10})$cycloalkyl, $(C_2\text{-}C_9)$heterocycloalkyl, $(C_6\text{-}C_{14})$ aryl, $(C_2\text{-}C_9)$heteroaryl, $(C_1\text{-}C_{10})$alkylamine, —O(O)C—$(C_1\text{-}C_{10})$alkyl, $(C_1\text{-}C_{10})$alkyl-COOH, $(C_3\text{-}C_{10})$cycloalkyl-COOH, —(O)$CH_3$, —OH, amide, a guanidino group represented by Formula (A)

(A)

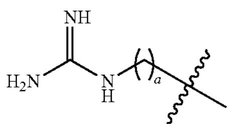

wherein a is an integer from 0 to 25, a guanidinium chloride group represented by Formula (B), (B)

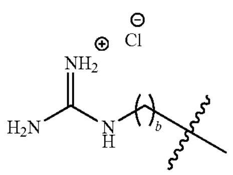

wherein b is an integer from 0 to 25, a guanidinobenzene group represented by Formula (C), (C)

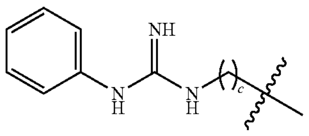

wherein c is an integer from 0 to 25, a dihydroxy group, represented by Formula (D), (D)

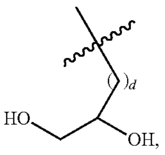

wherein d is an integer from 0 to 25, a polyethylene glycol group, represented by Formula (E)

(E)

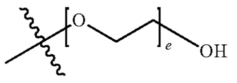

wherein e is an integer from 1 to 400, a group represented by Formula (F)

(F)

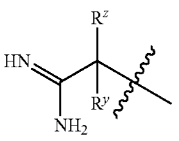

wherein $R^z$ and $R^y$ are each independently selected from a group consisting of H, $(C_1\text{-}C_{10})$alkyl, $(C_2\text{-}C_9)$heteroalkyl, $(C_3\text{-}C_{10})$cycloalkyl, $(C_2\text{-}C_9)$heterocycloalkyl, $(C_6\text{-}C_{14})$aryl, $(C_2\text{-}C_9)$heteroaryl, $(C_1\text{-}C_{10})$alkylamine, —O(O)C—$(C_1\text{-}C_{10})$alkyl, $(C_1\text{-}C_{10})$alkyl-COOH, $(C_3\text{-}C_{10})$cycloalkyl-COOH, —(O)$CH_3$, —OH, amide, or a group represented by Formula (G)

(G)

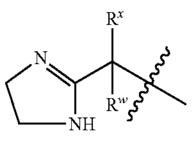

wherein $R^x$ and $R^w$ are each independently selected from a group consisting of H, $(C_1\text{-}C_{10})$alkyl, $(C_2\text{-}C_9)$heteroalkyl, $(C_3\text{-}C_{10})$cycloalkyl, $(C_2\text{-}C_9)$heterocycloalkyl, $(C_6\text{-}C_{14})$aryl, $(C_2\text{-}C_9)$heteroaryl, $(C_1\text{-}C_{10})$alkylamine, —O(O)C—$(C_1\text{-}C_{10})$alkyl, $(C_1\text{-}C_{10})$alkyl-COOH, $(C_3\text{-}C_{10})$cycloalkyl-COOH, —(O)$CH_3$, cyano, cyano$(C_1\text{-}C_{10})$alkyl, —OH, amide, or a point of attachment to another repeat unit of the copolymer.

The polydiallylamine copolymers of the instant invention may include varying ratios of the monomers represented by Formula (II) and Formula (III). For example, the ratio of Formula (II) monomer:Formula (III) monomer in the polydiallylamine copolymers is from 99:1 to 1:99. Further, the ratio of Formula (II) monomer:Formula (III) monomer in the polydiallylamine copolymers is from 90:10 to 5:95. More specifically, the ratio of Formula (II) monomer:Formula (III) monomer in the polydiallylamine copolymers is from 12.5:87.5 to 87.5:12.5. And in yet in another example, the ratio of Formula (II) monomer:Formula (III) monomer in the instant polydiallylamine copolymers is from 25:75 to 75:25.

The polydiallylamine copolymers of the instant invention may also be block copolymers. The block polydiallylamine copolymers comprise blocks of Formula (II) and blocks of Formula (III) in the same polymer chain. In one embodiment, the polydiallylamine copolymers are a block copolymer where the relative percentage of repeat units of Formula (II) are in a block of about 99% to about 1% repeat units and wherein the relative percentage of repeat units of Formula (III) are in a block of about 1% to about 99% repeat units. In another embodiment, the polydiallylamine copolymers are a block copolymer where the relative percentage of repeat units of Formula (II) are in a block of about 95% to about 5% repeat units and wherein the relative percentage of repeat units of Formula (III) are in a block of about 5% to about 95% repeat units. The block polydiallylamine copolymers of the instant invention may be crosslinked.

The polydiallylamine copolymers of the instant invention comprise two or more polymer chains. It is understood in the art that cross-linked polymers may be of a network of infinite polymer chains; these polymer molecules are cross-linked to each other to form a large molecule (*Text Book of Polymer Science, 2$^{nd}$* Edition).

In a preferred embodiment, the polydiallylamine copolymers comprise two to two million polymer chains. In another embodiment, the polydiallylamine copolymer comprises two to one million polymer chains. In yet another embodiment, the polydiallylaimen copolymer comprises two to five hundred thousand polymer chains. In still yet another embodiment, the polydiallylamine copolymer comprises two to two hundred fifty thousand polymer chains. And in yet another embodiment, the polydiallylamine copolymer comprises two to one hundred thousand polymer chains. In still another embodiment, the polydiallylamine copolymer comprises two to fifty thousand polymer chains. In another embodiment, the polydiallylamine copolymer comprises two to twenty five thousand polymer chains. In another embodiment, the polydiallyalamine copolymer comprises two to ten thousand polymer chains. In another embodiment, the polydiallylamine copolymer comprises two to five thousand polymer chains. In still another embodiment, the polydiallylamine copolymer comprises two to one five thousand polymer chains. And in yet another embodiment, the polydiallylamine copolymer comprises two to five hundred polymer chains. In another embodiment, the polydiallylamine copolymer comprises two to two hundred fifty polymer chains. And in another embodiment, the polydiallylamine copolymer comprises two to one hundred polymer chains. And in still another embodiment, the polydiallylamine copolymer comprises two to fifty polymer chains. In another embodiment, the polydiallyamine copolymer comprises two to twenty five polymer chains. In a preferred embodiment, the copolymer comprises two to ten polymer chains. In specific embodiments, the polydiallylamine copolymer comprises two polymer chains, three polymer chains, four polymer chains, five polymer chains or six polymer chains.

The polydiallylamine copolymers can be cross-linked with a cross-linking agent. The cross-linking of the polydiallylamine copolymer may be within a single chain of the copolymer, between two chains of the polymer, or preferably both within a single chain of the copolymer and between polymer chains.

When cross-linked, the polydiallylamine copolymers may be cross-linked with a multifunctional multivalent amine specific reagent. Preferred multifunctional multivalent amine specific reagents used to cross-link the polydiallylamine copolymers include those that comprise two or more electrophilic groups. Examples of multifunctional multivalent amine specific reagents with two or more electrophilic groups used in the crosslinking of the polydiallylamine copolymer include but are not limited to halides, aldehydes, ketones, acid halides, acid active esters, epoxides, acrylates, methacrylates, arylsulfonates, alkylsulfonates, and vinyl sulfones.

Preferred cross-linking agents used in the cross-linking of the instant polydiallylamine copolymers are selected from epichlorohydrin, epibromohydrin, (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol digylcidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy)diphenylmethane, bisphenol F diglycidyl ether, 1,4-bis(2',3'-epoxypropyl)perfluoro-n-butane, 2, 6-di(oxiran-2-ylmethyl)-1,2,3,5,6,7-hexahydropyrrolo[3,4-f]isoindol-1,3,5,7-tetraone, bisphenol A diglycidyl ether, ethyl 5-hydroxy-6,8-di(oxiran-2-ylmethyl)-4-oxo-4h-chromene-2-carbo xylate, bis[4-(2,3-epoxy-propylthio)phenyl]-sulfide, 1,3-bis(3-glycidoxypropyl)tetramethyldisiloxane, 9,9-bis[4-(glycidyloxy)phenyl]fluorene, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris[[3-(epoxypropoxy)propyl]dimethylsilyloxy]-1,3,5,7,9,11,14-heptacyclopentyltricyclo[7.3.3.15,11]heptasiloxane, 4,4'-methylenebis(N,N-diglycidylaniline), bis(halomethyl)benzene, bis(halomethyl)biphenyl and bis(halomethyl)naphthalene. A specifically preferred cross-linking agent used to cross-link the instant polydiallymine copolymers is epicholorhydrin or a residue thereof.

The polydiallylamine copolymers of the instant invention are preferably crosslinked, and the ratio of cross-linked repeat units:un-cross-linked repeat units is from 1:99 to 50:50.

This invention further relates to pharmaceutical compositions comprising polydiallylamine copolymers. The pharmaceutical compositions of the instant invention comprise a copolymer comprising a polymer chain according to Formula (I):

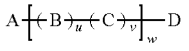

(I)

wherein:

u, and v are each independently an integer from 0 to 200,000; and w is an integer from 1 to 200,000, A, B, C and D are each independently repeat units selected from Formula (II) or Formula (III);

wherein Formula (II) is according to the structural formula:

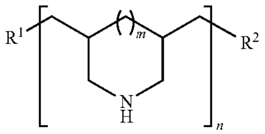

(II)

or a pharmaceutically acceptable salt thereof, wherein:

m is 0 or 1;

n is an integer from 1 to 200,000;

$R^1$ and $R^2$ are each independently a pharmaceutically acceptable end group or a point of attachment to another repeat unit of the copolymer;

and Formula (III) is according to the structural formula:

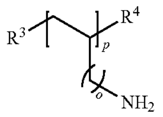

(III)

or a pharmaceutically acceptable salt thereof, wherein:

o is 0 or 1;

p is an integer from 1 to 200,000;

$R^3$ and $R^4$ are each independently a pharmaceutically acceptable end group or a point of attachment to another repeat unit of the copolymer;

with the provisio that the copolymer of Formula (I) is not exclusively a polymer of Formula (II) or exclusively a polymer of Formula (III)

and a pharmaceutically acceptable excipient.

The instant invention also relates to pharmaceutical compositions comprising polydiallylamine copolymers comprising two to two million polymer chains, wherein each polymer chain is according to Formula (I):

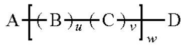

(I)

wherein:

u, and v are each independently an integer from 0 to 200,000; and w is an integer from 1 to 200,000, A, B, C and D are each independently repeat units selected from Formula (II) or Formula (III);

wherein Formula (II) is according to the structural formula:

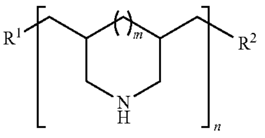

(II)

or a pharmaceutically acceptable salt thereof, wherein:

m is 0 or 1;

n is an integer from 1 to 200,000;

$R^1$ and $R^2$ are each independently a pharmaceutically acceptable end group or a point of attachment to another repeat unit of the copolymer;

and Formula (III) is according to the structural formula:

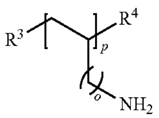

(III)

or a pharmaceutically acceptable salt thereof, wherein:

o is 0 or 1;

p is an integer from 1 to 200,000;

$R^3$ and $R^4$ are each independently a pharmaceutically acceptable end group or a point of attachment to another repeat unit of the copolymer;

and wherein:

(a) each polymer chain must be cross-linked with at least one other polymer chain, and (b) each polymer chain may be internally cross-linked;

and a pharmaceutically acceptable excipient.

The pharmaceutical compositions of the instant invention comprise the polydiallylamine copolymers described in the various embodiments above.

The polydiallylamine copolymers of the present invention may be administered alone or in a pharmaceutical composition comprising crosslinked polydiallylamine copolymers. Suitable pharmaceutical compositions may comprise polydiallylamine copolymer and one or more pharmaceutically acceptable excipients. The form in which the polydiallylamine copolymers or pharmaceutical compositions comprising a polydiallylamine copolymer are administered, for example, powder, tablet, capsule, solution, or emulsion, depends in part on the route by which it is administered. The polydiallylamine copolymers or pharmaceutical compositions comprising a polydiallylamine copolymer can be administered, for example, topically, orally, intranasally, by aerosol or rectally. Suitable excipients include, but are not limited to, are inorganic or organic materials such as gelatin, albumin, lactose, starch, stabilizers, melting agents, emulsifying agents, salts and buffers. Suitable pharmaceutically acceptable excipients for topical formulations such as ointments, creams and gels include, but are not limited to, commercially available inert gels or liquids supplemented with albumin, methyl cellulose, or a collagen matrix.

Although specific embodiments of the present disclosure will now be described with reference to the examples, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

All pharmaceutically acceptable salts, prodrugs, tautomers, hydrates and solvates of the compounds presently disclosed are also within the scope of the present disclosure.

Presently disclosed compounds that are basic in nature are generally capable of forming a wide variety of different salts with various inorganic and/or organic acids. Although such salts are generally pharmaceutically acceptable for administration to animals and humans, it is often desirable in practice to initially isolate a compound from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds can be readily prepared using conventional techniques, e.g., by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained.

Acids which can be used to prepare the pharmaceutically acceptable acid addition salts of the base compounds are those which can form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Presently disclosed compounds that are acidic in nature, e.g., contain a COOH or tetrazole moiety, are generally capable of forming a wide variety of different salts with various inorganic and/or organic bases. Although such salts are generally pharmaceutically acceptable for administration to animals and humans, it is often desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations, and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields of the desired solid salt.

Bases which can be used to prepare the pharmaceutically acceptable base addition salts of the base compounds are those which can form non-toxic base addition salts, i.e., salts containing pharmacologically acceptable cations, such as, alkali metal cations (e.g., potassium and sodium), alkaline earth metal cations (e.g., calcium and magnesium), ammonium or other water-soluble amine addition salts such as N-methylglucamine-(meglumine), lower alkanolammonium and other such bases of organic amines.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts and prodrugs thereof, can be prepared by any means known in the art.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

The compounds, salts, prodrugs, hydrates, and solvates presently disclosed can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of the present disclosure.

Atropisomers are also within the scope of the present disclosure. Atropisomers refer to compounds that can be separated into rotationally restricted isomers.

The present disclosure also provides pharmaceutical compositions comprising at least one presently disclosed compound and at least one pharmaceutically acceptable carrier. The pharmaceutically acceptable carrier can be any such carrier known in the art including those described in, for example, Remington's Pharmaceutical Sciences, Mack Publishing Co., (A. R. Gennaro edit. 1985). Pharmaceutical compositions of the compounds presently disclosed may be prepared by conventional means known in the art including, for example, mixing at least one presently disclosed compound with a pharmaceutically acceptable carrier.

Presently disclosed pharmaceutical compositions can be used in an animal or human. Thus, a presently disclosed compound can be formulated as a pharmaceutical composition for oral, buccal, parenteral (e.g., intravenous, intramuscular or subcutaneous), topical, rectal or intranasal administration or in a form suitable for administration by inhalation or insufflation.

The compounds presently disclosed may also be formulated for sustained delivery according to methods well known to those of ordinary skill in the art. Examples of such formulations can be found in U.S. Pat. Nos. 3,119,742, 3,492,397, 3,538,214, 4,060,598, and 4,173,626.

For oral administration, the pharmaceutical composition may take the form of, for example, a tablet or capsule prepared by conventional means with a pharmaceutically acceptable excipient(s) such as a binding agent (e.g., pregelatinized maize starch, polyvinylpyrrolidone or hydroxypropyl methylcellulose); filler (e.g., lactose, microcrystalline cellulose or calcium phosphate); lubricant (e.g., magnesium stearate, talc or silica); disintegrant (e.g., potato starch or sodium starch glycolate); and/or wetting agent (e.g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use. Such liquid preparations may be prepared by conventional means with a pharmaceutically acceptable additive(s) such as a suspending agent (e.g., sorbitol syrup, methyl cellulose or hydrogenated edible fats); emulsifying agent (e.g., lecithin or acacia); non-aqueous vehicle (e.g., almond oil, oily esters or ethyl alcohol); and/or preservative (e.g., methyl or propyl p-hydroxybenzoates or sorbic acid).

For buccal administration, the composition may take the form of tablets or lozenges formulated in a conventional manner.

Presently disclosed compounds may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent recognized by those of skill in the art. Alternatively, the active ingredient may be in powder form for reconstitution with a suitable vehicle, e.g., sterile pyrogen-free water, before use.

For topical administration, a presently disclosed compound may be formulated as an ointment or cream.

Presently disclosed compounds may also be formulated in rectal compositions such as suppositories or retention enemas, e.g., containing conventional suppository bases such as cocoa butter or other glycerides.

For intranasal administration or administration by inhalation, presently disclosed compounds may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the presently disclosed compound. Capsules and cartridges (made, for example, from gelatin) for use in an inhaler or insufflator may be formulated containing a powder mix of a presently disclosed compound and a suitable powder base such as lactose or starch.

The polydiallylamine copolymers may be administered as a pharmaceutical composition. The polydiallylamine copolymers and pharmaceutical compositions comprising polydiallylamine copolymers may be administered once per day up to three times per day. These pharmaceutical compositions comprising polydiallylamine copolymers are administered in an effective amount at an appropriate dosing schedule to achieve the desired therapeutic effect. The skilled artisan will be able to determine the effective amount and dosing frequency of the polydiallylamine copolymers depending on the individual and the condition being treated.

Pharmaceutical compositions and methods of treatment or prevention comprising administering prodrugs of at least one presently disclosed compound are also within the scope of the present disclosure.

This invention also relates to methods of treating type 2 diabetes in a subject in need thereof comprising administering to the subject a polydiallylamine copolymer or a pharmaceutical composition comprising a polydiallylamine copolymer. The instant invention further relates to methods of treating type 2 diabetes in a subject, wherein the subject soffers from decreased renal function, comprising administering to the subject a polydiallylamine copolymer or a pharmaceutical composition comprising a polydiallylamine copolymer. More particularly, the instant invention relates to methods of treating type 2 diabetes in a subject in need thereof, where the subject suffers from an additional comorbid condition including but not limited to chronic kidney disease (CKD), comprising administering to the subject a polydiallylamine copolymer or a pharmaceutical composition comprising a polydiallylamine copolymer. The invention further relates to a method of treating type 2 diatetes in a subject also suffering from hyperphosphatemia associated with CKD.

The invention further relates to methods of treating type 2 diabetes in a subject in need thereof comprising administering to the subject a polydiallylamine copolymer or a pharmaceutical composition comprising a polydiallylamine copolymer, further comprising administering to the subject one or more additional agents selected from the group consisting of a biguanide, a sulfonyl urea, a dipeptidyl peptidase inhibitor, a peroxisome proliferator-activated receptors agonist, a dual peroxisome proliferator-activated receptors agonists, a sodium-dependent glucose cotransporter inhibitor, an ileal bile acid transporter inhibitor, insulin, an insulin analog, a glucagon-like peptide-1 agonist, a dual agonist, an alpha glucosidase inhibitor, and an amylin analog. The instant invention further to methods of treating type 2 diabetes in a subject in need thereof comprising administering to the subject a polydiallylamine copolymer or a pharmaceutical composition comprising a polydiallylamine copolymer, further comprising administering to the subject one or more beta cell and beta cell forming therapies.

The invention also relates to methods of mitigating the complications of type 2 diabetes in a subject in need thereof comprising administering to the subject a polydiallylamine copolymer or a pharmaceutical composition comprising a polydiallylamine copolymer. The invention further relates to methods of mitigating the complications of type 2 diabetes in a subject in need thereof comprising administering to the subject a polydiallylamine copolymer or a pharmaceutical composition comprising a polydiallylamine copolymer, further comprising administering to the subject one or more additional agents selected from the group consisting of 3-hydroxy-3-methylglutaryl coenzyme A reductase inhibitor, fibrate, niacin, cholesterol absorption inhibitor, pancreatic lipase inhibitor, 5-$HT_{2C}$ receptor agonist, phosphate transport inhibitor, alkaline phosphatase inhibitor, bile acid sequestrant, vitamin D analog, or a calcium sensing receptor activator (calcimimetic).

The instant invention also relates to methods of reducing blood glucose in a subject in need thereof comprising administering to the subject comprising administering to the subject a polydiallylamine copolymer or a pharmaceutical composition comprising a polydiallylamine copolymer.

The subject invention further relates to methods of reducing blood hemoglobin A1c in a subject in need thereof comprising administering to the subject comprising administering to the subject a polydiallylamine copolymer or a pharmaceutical composition comprising a polydiallylamine copolymer.

The instant invention relates to methods of improving insulin resistance in a subject in need thereof comprising administering to the subject comprising administering to the subject a polydiallylamine copolymer or a pharmaceutical composition comprising a polydiallylamine copolymer.

The instant invention also relates to methods of improving lipid profile in a subject in need thereof comprising administering to the subject comprising administering to the subject a polydiallylamine copolymer or a pharmaceutical composition comprising a polydiallylamine copolymer.

The instant invention further relates to methods of reducing LDL cholesterol in a subject in need thereof comprising administering to the subject a polydiallylamine copolymer or a pharmaceutical composition comprising a polydiallylamine copolymer.

The instant invention relates to methods of reducing total cholesterol in a subject in need thereof comprising administering to the subject a polydiallylamine copolymer or a pharmaceutical composition comprising a polydiallylamine copolymer.

The instant invention also relates to methods of lowering elevated lipids in a subject in need thereof comprising administering to the subject a polydiallylamine copolymer or a pharmaceutical composition comprising a polydiallylamine copolymer.

The instant invention further relates to methods of binding dietary lipids in a subject in need thereof comprising administering to the subject a polydiallylamine copolymer or a pharmaceutical composition comprising a polydiallylamine copolymer.

The instant invention relates to methods of lowering uremic toxins comprising in a subject in need thereof comprising administering to the subject a polydiallylamine copolymer or a pharmaceutical composition comprising a polydiallylamine copolymer.

The instant invention also relates to methods of reducing serum phosphorous in a subject in need thereof comprising administering to the subject a polydiallylamine copolymer or a pharmaceutical composition comprising a polydiallylamine copolymer.

The instant invention further relates to methods of reducing absorption of dietary phosphate in a subject in need thereof comprising administering to the subject a polydiallylamine copolymer or a pharmaceutical composition comprising a polydiallylamine copolymer.

The instant invention relates to methods of binding AGE precursors in a subject in need thereof comprising administering to the subject a polydiallylamine copolymer or a pharmaceutical composition comprising a polydiallylamine copolymer.

The instant invention also relates to methods of binding dietary dicarbonyls in a subject in need thereof comprising administering to the subject a polydiallylamine copolymer or a pharmaceutical composition comprising a polydiallylamine copolymer.

The instant invention further relates to methods of reducing oxidative stress in a subject in need thereof comprising administering to the subject a polydiallylamine copolymer or a pharmaceutical composition comprising a polydiallylamine copolymer.

The instant invention relates to methods of binding bile acids in a subject in need thereof comprising administering to the subject a polydiallylamine copolymer or a pharmaceutical composition comprising a polydiallylamine copolymer.

The instant invention also relates to methods of reducing body fat in a subject in need thereof comprising administering to the subject a polydiallylamine copolymer or a pharmaceutical composition comprising a polydiallylamine copolymer.

The instant invention further relates to methods of reducing inflammation parameters in a subject in need thereof comprising administering to the subject a polydiallylamine copolymer or a pharmaceutical composition comprising a polydiallylamine copolymer.

The polydiallylamine copolymers and pharmaceutical compositions comprising polydiallylamine copolymers can be administered alone or in combination with one or more additional drugs. Additional drugs administered in combination with the polydiallylamine copolymers and pharmaceutical compositions comprising polydiallylamine copolymers of the present invention include other agents intended to compounds, including those used in the treatment of type 2 diabetes and those used to mitigate the risks of type 2 diabetes.

The additional agents may be administered concomitantly with the polydiallylamine copolymer or pharmaceutical compositions comprising polydiallylamine copolymers. The additional agents may also be administered in series with the polydiallylamine copolymer or pharmaceutical compositions comprising polydiallylamine copolymers. The pharmaceutical composition comprising polydiallylamine copolymers may also further comprise an agent used for the treatment of type 2 diabetes.

Examples of other drugs for treating of type 2 diabetes that can be used with the polydiallylamine copolymers and pharmaceutical compositions comprising polydiallylamine copolymers of the instant invention include biguanides, sulfonyl ureas, dipeptidyl peptidase (DDP-IV) inhibitors, peroxisome proliferator-activated receptors (PPAR) agonists, dual PPAR agonists, sodium-dependent glucose cotransporters (SGLT) inhibitors, ileal bile acid transporter (IBAT) inhibitors, insulin, insulin analogs, glucagon-like peptide-1 (GLP-1) agonists, dual GLP-1 and glucose-dependent insulinotropic polypeptide (GIP) agonists, alpha glucosidase inhibitors, and amylin analogs.

Examples of biguanidines include but are not limited to metformin and phenformin. Examples of sulfonyl ureas include but are not limited to acetohexamide, carbutamide, chloropropamide, metahexamide, tolbutamide, tolazamide, glibenclamide, blibornuride, glipizide, gliquidone, glisoxepide, glyclopyramide, glimepiride, and gliclazide. Examples of DDP-IV inhibitors include but are not limited to alogliptin, anagliptin, gemigliptin, lingaliptin, saxagliptin, sitagliptin, teneligliptin, and vildagliptin. Examples of PPAR agonists include but are not limited to pioglitazone, rivoglitazone, rosiglitazone, and troglitazone. Examples of dual PPAR agonists include but are not limited to aleglitazar, muraglitazar, saroglitazar, and tesaglitazar. Examples of SGLT inhibitors include but are not limited to canagliflozin, dapagliflozin, empagliflozin, remogliflozin, sergliflozin, and tofogliflozin. Examples of IBAT inhibitors include but are not limited to elobixibat and (3R,5R)-3-butyl-3-ethyl-7,8-dimethoxy-5-phenyl-4,5-dihydro-2H-benzo[f][1,4]thiazepine 1,1-dioxide. Examples of insulin analogs include but are not limited to insulin lispro, insulin aspart, insulin glulisine, insulin glargine, insulin detemir, insulin degludec, and inhalable insulin. Examples of GLP-1 agonists include but are not limited to exenatide, liraglutide, taspoglutide, albiglutide, lixisenatide, dualglutide, and semaglutide. Examples of dual GLP-1/GIP agonists include but are not limited to Y(1)-dA(2)-I(12)-N(17)-V(18)-I(27)-G(28,29)-glucagon (YAG-glucagon). Examples of alpha glucosidase inhibitors include but are not limited to acarabse, miglitol and voglibose. An example of an amylin analog includes but is not limited to pramlintide.

Examples of other drugs for mitigating the risks associated with type 2 diabetes include that can be used with the polydiallylamine copolymers and pharmaceutical compositions comprising polydiallylamine copolymers of the instant invention include β-hydroxy-β-methylglutaryl coenzyme A (HMG-CoA) reductase inhibitors (statins), fibrates (peroxisome proliferator-activated receptor-alpha [PPARα] agonists), niacin and niacin derivatives, cholesterol absorption inhibitors, pancreatic lipase inhibitors, 5-$HT_{2C}$ receptor agonists, phosphate transport inhibitors, alkaline phosphatase inhibitors, bile acid sequestrants, vitamin D analogs, or a calcium sensing receptor activators (calcimimetics).

Examples of statins include but are not limited to atorvastatin, cerivastatin, fluvastatin, lovastatin, mevastatin, pitavastatin, pravastatin, rosuvastatin, and simvastatin. Examples of fibrates include but are not limited to bezafibrate, ciprofibrate, clofibrate, gemfibrozil, and fenofibrate. Examples of niacin and niacin derivateives include niceritrol, niacin, nicofuranose, aluminum nicotinate, nicotinyl alcohol and acipimox. Examples of cholesterol absorption inhibitors include but are not limited to exetimibe and (3R,4S)-1,4-bis(4-methoxyphenyl)-3-(3-phenylpropyl)-2-azetidinone. An example of pancreatic lipase inhibitor includes but is not limited to orlistat. An example of a 5-$HT_{2C}$ receptor agonist includes but is not limited to lorcaserin. An example of a phosphate transport inhibitor includes but is not limited to niacin. An example of alkaline phosphatase inhibitor includes but is not limited to vanadate. Examples of bile acid sequestrants include but are not limited to cholestyramine, colestipol, colestilan, colextran, and colesevelam. Examples of vitamin D analogs include but are not limited to calcitriol, dihydrotachysterol, doxercalciferol and paricalcitol. An example of a calcimimitic includes but is not limited to cinacalcet.

The number of repeat units and the molecular weight of the polydiallylamine copolymers of the instant inventions are controlled by synthesis of the compound. Preferred polydiallyamine copolymers of the invention are presented in the Examples below. The methods of synthesis for the starting polymers of Formula (I), polydiallylamine, the starting polymers of Formula (II), polyallylamine or polyvinylamine, and the crosslinking agents, which are used as intermediates for the preparation of these copolymer networks, are known in the literature. The polydiallylamine copolymer networks disclosed in this invention are novel compositions. Methods of preparing preferred polydiallylamine copolymers of the invention and controlling for the number of repeat units and molecular weight are described in Example 1.

EXAMPLES

Example 1

Synthesis of Crosslinked Polydiallylamine Copolymers

Example 1

1: Synthesis of Crosslinked Polydiallylamine-Polyvinylamine (PDA-PVAm) Copolymers A total of nineteen (19) crosslinked copolymers containing polydiallylamine and polyvinylamine were synthesized according to the methods set forth below. The PDA-PVAm copolymers were characterized by various methods such elemental analysis (carbon to nitrogen mole ratio), potentiometric titration (to estimate amine content), swelling index, presence of carbonate counterion (by thermogravimetric analysis) etc. The results for the polymers in Example 1-1-1 to Example 1-1-5 are presented in Table 1; the results for the polymers in Example 1-1-6 to Example 1-1-19 are presented in Table 2.

Example 1

1-1: PDA-PVAm (12.5:87.5 mole/mole) Copolymer

In a 250 ml, 3-necked round bottom flask fitted with overhead stirring were taken 10.64 g of 50% (w/w) aqueous solution of poly(diallylamine-HCl), 77.92 g of 15.4% (w/w) aqueous solution of poly(vinylamine) and 84.64 g of deionized water. After stirring the polymer solution for 14 hours, the pH of reaction mixture was adjusted to 10.8 by adding appropriate amount of 1.0 N HCl. While stirring, 1.25 ml of epichlorohydrin was added to the polymer solution. The stirring continued until the solution became a gel. At that point the stirring was discontinued and the reaction mixture was left at 25° C. for 48 hours. The resulting polymer gel was broken into small pieces. To these broken gel particles was added 500 ml deionized water and the suspension was blended for 15 seconds using a 700S Waring Blender. The resulting suspension was mixed with 1 L of deionized water and stirred for 15 minutes. The pH of the suspension was adjusted to 12.80 using 50% (w/w) aqueous NaOH and stirred for 15 minutes. The suspension was filtered. The filtered gel mixed with 2 L of deionized water and the suspension was stirred for 15 minutes. After filtration, the gel was dispersed into 3 L of deionized water and stirred for 15 minutes. The suspension was bubbled with CO2 gas until the pH of the suspension was 8.0. After filtration, the isolated gel was dried at 60° C. in a forced air oven for 18 hours yielding 19.23 g of the polymer as an off white solid.

Example 1

1-2: PDA-PVAm (25:75 mole/mole) Copolymer

In a 250 ml, 3-necked round bottom flask fitted with overhead stirring were taken 18.0 g of 50% (w/w) aqueous solution of poly(diallylamine-HCl), 56.5 g of 15.4% (w/w)

aqueous solution of poly(vinylamine), and 102.5 g of deionized water. After stirring the polymer solution for 14 hours, the pH of reaction mixture was adjusted to 10.7 by adding appropriate amount of 50% (w/w) aqueous NaOH. While stirring, 1.05 ml of epichlorohydrin was added to the polymer solution. The stirring continued until the solution became a gel. At that point the stirring was discontinued and the reaction mixture was left at 25° C. for 48 hours. The resulting polymer gel was broken into small pieces. To these broken gel particles was added 500 ml deionized water and the suspension was blended for 15 seconds using a 700S Waring Blender. The resulting suspension was mixed with 1 L of deionized water and stirred for 15 minutes. The pH of the suspension was adjusted to 12.80 using 50% (w/w) aqueous NaOH and stirred for 15 minutes. The suspension was filtered. The filtered gel mixed with 2 L of deionized water and the suspension was stirred for 15 minutes. After filtration, the gel was dispersed into 3 L of deionized water and stirred for 15 minutes. The suspension was bubbled with CO2 gas until the pH of the suspension was 8.0. After filtration, the isolated gel was dried at 60° C. in a forced air oven for 18 hours yielding 14.8 g of the polymer as an off white solid.

Example 1

1-3: PDA-PVAm (50:50 mole/mole) Copolymer

In a 250 ml, 3-necked round bottom flask fitted with overhead stirring were taken 26.0 g of 50% (w/w) aqueous solution of poly(diallylamine-HCl), 27.2 g of 15.4% (w/w) aqueous solution of poly(vinylamine) and 118.7 g of deionized water. After stirring the polymer solution for 14 hours, the pH of reaction mixture was adjusted to 10.5 by adding appropriate amount of 50% (w/w) aqueous NaOH. While stirring, 0.76 ml of epichlorohydrin was added to the polymer solution. The stirring continued until the solution became a gel. At that point the stirring was discontinued and the reaction mixture was left at 25° C. for 48 hours. The resulting polymer gel was broken into small pieces. To these broken gel particles was added 500 ml deionized water and the suspension was blended for 15 seconds using a 700S Waring Blender. The resulting suspension was mixed with 1 L of deionized water and stirred for 15 minutes. The pH of the suspension was adjusted to 12.80 using 50% (w/w) aqueous NaOH and stirred for 15 minutes. The suspension was filtered. The filtered gel mixed with 2 L of deionized water and the suspension was stirred for 15 minutes. After filtration, the gel was dispersed into 3 L of deionized water and stirred for 15 minutes. The suspension was bubbled with CO2 gas until the pH of the suspension was 8.0. After filtration, the isolated gel was dried at 60° C. in a forced air oven for 18 hours yielding 12.9 g of the polymer as an off white solid.

Example 1

1-4: PDA-PVAm (75:25 mole/mole) Copolymer

In a 250 ml, 3-necked round bottom flask fitted with overhead stirring were taken 32.0 g of 50% (w/w) aqueous solution of poly(diallylamine-HCl), 11.17 g of 15.4% (w/w) aqueous solution of poly(vinylamine) and 129 g of deionized water. After stirring the polymer solution for 14 hours, the pH of reaction mixture was adjusted to 10.6 by adding appropriate amount of 50% (w/w) aqueous NaOH. While stirring, 0.62 ml of epichlorohydrin was added to the polymer solution. The stirring continued until the solution became a gel. At that point the stirring was discontinued and the reaction mixture was left at 25° C. for 48 hours. The resulting polymer gel was broken into small pieces. To these broken gel particles was added 500 ml deionized water and the suspension was blended for 15 seconds using a 700S Waring Blender. The resulting suspension was mixed with 1 L of deionized water and stirred for 15 minutes. The pH of the suspension was adjusted to 12.80 using 50% (w/w) aqueous NaOH and stirred for 15 minutes. The suspension was filtered. The filtered gel mixed with 2 L of deionized water and the suspension was stirred for 15 minutes. After filtration, the gel was dispersed into 3 L of deionized water and stirred for 15 minutes. The suspension was bubbled with CO2 gas until the pH of the suspension was 8.0. After filtration, the isolated gel was dried at 60° C. in a forced air oven for 18 hours yielding 11.34 g of the polymer as an off white solid.

Example 1

1-5: PDA:PVAm (87.5:12.5 mole/mole) Copolymer

In a 250 ml, 3-necked round bottom flask fitted with overhead stirring were taken 34.0 g of 50% (w/w) aqueous solution of poly(diallylamine-HCl), 5.1 g of 15.4% (w/w) aqueous solution of poly(vinylamine) and 129 g of deionized water. After stirring the polymer solution for 14 hours, the pH of reaction mixture was adjusted to 10.5 by adding appropriate amount of 50% (w/w) aqueous NaOH. While stirring, 0.57 ml of epichlorohydrin was added to the polymer solution. The stirring continued until the solution became a gel. At that point the stirring was discontinued and the reaction mixture was left at 25° C. for 48 hours. The resulting polymer gel was broken into small pieces. To these broken gel particles was added 500 ml deionized water and the suspension was blended for 15 seconds using a 700S Waring Blender. The resulting suspension was mixed with 1 L of deionized water and stirred for 15 minutes. The pH of the suspension was adjusted to 12.80 using 50% (w/w) aqueous NaOH and stirred for 15 minutes. The suspension was filtered. The filtered gel mixed with 2 L of deionized water and the suspension was stirred for 15 minutes. After filtration, the gel was dispersed into 3 L of deionized water and stirred for 15 minutes. The suspension was bubbled with CO2 gas until the pH of the suspension was 8.0. After filtration, the isolated gel was dried at 60° C. in a forced air oven for 18 hours yielding 9.2 g of the polymer as an off white solid.

TABLE 1

Characterization Results of Crosslinked Polydiallylamine-Polyvinylamine (PDA-PVAm) Copolymers

| PDA-PVAm Copolymer | PDA:PVAm (mole:mole) | Total Titratable Amines (mmol/g) | Swelling Index | $CO_3$ % |
|---|---|---|---|---|
| Example 1-1-1 | 87.5:12.5 | 12.205 | 10.5 | 20.36 |
| Example 1-1-2 | 75:25 | 9.238 | 14.4 | 19 53 |
| Example 1-1-3 | 50:50 | 7.449 | 23.3 | 18.19 |
| Example 1-1-4 | 25:75 | 7.942 | 30.8 | 18.26 |
| Example 1-1-5 | 12.5:87.5 | 8.72 | 38 | 17.09 |

Synthesis of Additional Crosslinked Poly(Diallylamine)-Poly(Vinylamine) (PDA:PVAm) Copolymers A total of fourteen (14) crosslinked copolymers containing polydiallylamine and polyallylamine were synthesized under varying reaction parameters including the ratio of polydiallylamine to polyallylamine, amount of crosslinking agent, concentration of the polymer solution, and reaction temperature. A general procedure for the syntheses of these copolymers is provided below. Specific details about the experimental parameters and their molecular characterization results are summarized in Table 2 below.

Appropriate amounts of polydiallylamine hydrochloride (PDA.HCl) and polyvinylamine (PVAm) were taken in a 500 mL round bottomed flask. The desired concentrations of the polymer solutions were adjusted by adding appropriate amounts of deionized water. After achieving the desired concentration, the pH of the solutions were adjusted to the desired level by addition of NaOH pellets and allowed to cool to 25° C. To this rapidly stirred polymer solution, an appropriate amount of crosslinking agent (epichlorohydrin) was added and the reaction mixture was stirred 30 seconds. While stirring, the temperature was raised to desired level. After a gel was formed, the stirring was discontinued and the reaction mixture was allowed stand at 25° C. for 24 hours under reduced pressure. The gel was broken into small pieces and pushed through a 2000 mm sieve to produce uniform particles. The polymer particles were suspended in deionized water and the pH of the suspension was adjusted to 13 by the addition of NaOH pellets, stirred for 10 minutes, and filtered. The gel particles were subjected a series of washing and filtration steps until the conductivity of the suspension reached a value of ≤200 $mScm^{-1}$. The polymer suspensions were bubbled with appropriate amounts of $CO_2$ gas to achieved desired levels of carbonate. The gel particles were subsequently filtered and dried at 60° C. under reduced pressure to constant weight.

TABLE 2

Reaction Conditions and Characterization Results of Crosslinked Polydiallylamine-Polyvinylamine (PDA-PVAm) Copolymers

| PDA:PVAm Crosslinked Copolymers | PDA:PVAm (mole:mole) | PVAm (g) | PDA (g) | Mole % 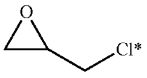 | Swelling Index |
|---|---|---|---|---|---|
| Example 1- 1- 6 | 1:3 | 3.93 | 4.07 | 10 | 4.5 |
| Example 1- 1- 7 | 1:10 | 6.11 | 1.89 | 10 | 7.5 |
| Example 1- 1- 8 | 1:3 | 3.93 | 4.07 | 10 | 8.2 |
| Example 1- 1- 9 | 1:10 | 6.11 | 1.89 | 10 | 10.3 |
| Example 1- 1- 10 | 1:3 | 3.93 | 4.07 | 10 | 7.1 |
| Example 1- 1- 11 | 1:10 | 6.11 | 1.89 | 10 | 9.6 |
| Example 1- 1- 12 | 1:3 | 3.93 | 4.07 | 20 | 2.1 |
| Example 1- 1- 13 | 1:10 | 6.11 | 1.89 | 20 | 3.7 |
| Example 1- 1- 14 | 1:3 | 3.93 | 4.07 | 20 | 4.4 |
| Example 1- 1- 15 | 1:10 | 6.11 | 1.89 | 20 | 6.0 |
| Example 1- 1- 16 | 1:3 | 3.93 | 4.07 | 20 | 5.6 |
| Example 1- 1- 17 | 1:10 | 6.11 | 1.89 | 20 | 4.6 |

TABLE 2-continued

Reaction Conditions and Characterization Results of Crosslinked Polydiallylamine-Polyvinylamine (PDA-PVAm) Copolymers

| PDA:PVAm Crosslinked Copolymers | PDA:PVAm (mole:mole) | PVAm (g) | PDA (g) | Mole % 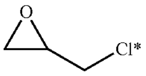 | Swelling Index |
|---|---|---|---|---|---|
| Example 1- 1- 18 | 1:6.5 | 5.42 | 2.58 | 15 | 5.6 |
| Example 1- 1- 19 | 1:6.5 | 5.42 | 2.58 | 15 | 8.4 |

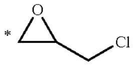 (epichlorohydrin), crosslinking agent; mol % with respect to total polymer

Example 1

2: Synthesis of Crosslinked Polydiallylamine-Polyallylamine (PDA-PAA) Copolymers A total of nineteen (19) crosslinked copolymers containing polydiallylamine and polyallylamine were synthesized under varying reaction parameters including the ratio of polydiallylamine to polyallylamine, amount of crosslinking agent, concentration of the polymer solution, and reaction temperature. A general procedure for the syntheses of these copolymers is provided below. Specific details about the experimental parameters including the amounts of different reagents used, temperature, pH and molecular characterization results are summarized in Table 3 below.

Appropriate amounts of polydiallylamine hydrochloride (PDA.HCl) and polyallylamine hydrochloride (PAA.HCl) were taken in a 500 mL round bottomed flask. The desired concentrations of the polymer solutions were adjusted by adding appropriate amounts of deionized water. After achieving the desired concentration, the pH of the solutions were adjusted to the desired level by addition of NaOH pellets and allowed to cool to 25° C. To this rapidly stirred polymer solution, an appropriate amount of crosslinking agent (epichlorohydrin) was added and the reaction mixture was stirred 30 seconds. While stirring, the temperature was raised to desired level. After a gel was formed, the stirring was discontinued and the reaction mixture was allowed stand at 25° C. for 24 hours under reduced pressure. The gel was broken into small pieces and pushed through a 2000 mm sieve to produce uniform particles. The polymer particles were suspended in deionized water and the pH of the suspension was adjusted to 13 by the addition of NaOH pellets, stirred for 10 minutes, and filtered. The gel particles were subjected a series of washing and filtration steps until the conductivity of the suspension reached a value of ≤200 $mScm^{-1}$. The polymer suspensions were bubbled with appropriate amounts of $CO_2$ gas to achieved desired levels of carbonate. The gel particles were subsequently filtered and dried at 60° C. under reduced pressure to constant weight.

TABLE 3

Reaction Conditions and Characterization Results of Crosslinked Polydiallylamine-Polyallylamine (PDA-PAA) Copolymers

| PDA-PAA Copolymer | PDA.HCl (g) | PAA.HCl (g) | Reaction Temp (° C.) | pH | [Total polymer] (wt %) | 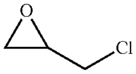 (g) | % $CO_3$ | Swell Index | Total Titratable Amines (mmol/g) |
|---|---|---|---|---|---|---|---|---|---|
| Example 1-2-1 | 2.1 | 12.6 | 60 | 12.0 | 35 | 1.80 | 17.53 | 9.9 | 10.59 |
| Example 1-2-2 | 2.1 | 12.6 | 60 | 12.0 | 35 | 1.80 | 20.99 | 8.5 | 10.39 |
| Example 1-2-3 | 5.7 | 7.98 | 40 | 13.0 | 45 | 2.74 | 2.82 | 2.2 | 7.86 |
| Example 1-2-4 | 1.36 | 13.6 | 40 | 13.0 | 25 | 0.67 | 4.11 | 21 | 13.23 |
| Example 1-2-5 | 5.7 | 7.98 | 80 | 11.0 | 25 | 2.74 | 2.39 | 4.2 | 8.49 |
| Example 1-2-6 | 1.36 | 13.6 | 80 | 13.0 | 25 | 2.99 | 2.89 | 4.4 | 11.95 |
| Example 1-2-7 | 1.36 | 13.6 | 40 | 13.0 | 45 | 0.67 | 13.37 | 8.5 | 11.8 |
| Example 1-2-8 | 5.7 | 7.98 | 40 | 11.0 | 45 | 0.62 | 22.98 | 7.2 | 10.27 |
| Example 1-2-9 | 5.7 | 7.98 | 80 | 13.0 | 25 | 0.62 | 21.45 | 12.8 | 8.9 |
| Example 1-2-10 | 5.7 | 7.98 | 80 | 11.0 | 45 | 2.74 | 9.06 | 1.9 | 8.15 |
| Example 1-2-11 | 5.7 | 7.98 | 40 | 11.0 | 25 | 0.62 | 8.82 | 13.5 | 11.27 |
| Example 1-2-12 | 1.36 | 13.6 | 80 | 13.0 | 45 | 2.99 | 16.66 | 3 | 9.34 |
| Example 1-2-13 | 5.7 | 7.98 | 80 | 13.0 | 45 | 0.62 | 2.3 | 9.2 | 10.19 |
| Example 1-2-14 | 1.36 | 13.6 | 40 | 11.0 | 45 | 2.99 | 2.52 | 4.5 | 12.37 |
| Example 1-2-15 | 5.7 | 7.98 | 40 | 13.0 | 25 | 2.74 | 11.16 | 4.3 | 7.91 |
| Example 1-2-16 | 1.36 | 13.6 | 80 | 11.0 | 45 | 0.679 | 2.57 | 11.4 | 12.36 |
| Example 1-2-17 | 1.36 | 13.6 | 40 | 11.0 | 25 | 2.99 | 19.09 | 4.1 | 10.27 |
| Example 1-2-18 | 1.36 | 13.6 | 80 | 11.0 | 25 | 0.67 | 26.13 | 9.1 | 10.5 |
| Example 1-2-19 | 2.1 | 12.6 | 60 | 12.0 | 35 | 1.8 | 14.38 | 5.2 | 9.98 |

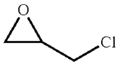
(epichlorohydrin), crosslinking agent

Example 2

In Vitro Studies

Example 2

1: In Vitro Phosphate Binding Properties of Crosslinked PDA-PVAm and PDA-PAA Copolymers Phosphate binding properties of crosslinked PDA-PVAm and PDA-PAA copolymers were determined under in vitro conditions. Into a pre-labeled 50 mL centrifuge tube was added pre-weighed amount of the polymer. The weight of the polymer sample was corrected for loss on drying (which was measured by thermogravimetric analysis (TGA) method). To the polymer containing centrifuge tube was added 20 mL of the phosphate solution of appropriate concentration (prepared by dissolving $KH_2PO_4$ in BES buffer at pH 7.0). The centrifuge tube containing the polymer suspension was slowly shaken at 37° C. for 2 hours using an orbital shaker. The polymer suspension was filtered using a 3 mL syringe fitted with a 0.45 μm Supor Acrodisc syringe filter. The filtrate was collected and phosphate content in the filtrate was estimated by ion chromatography using a standard curve generated from the stock phosphate solutions of known concentrations. The unbound phosphate values were used to calculate polymer bound phosphate.

Example 2

2: In Vitro Bile Acid Binding Properties of Crosslinked PDA-PVAm and PDA-PAA Copolymers Bile acid binding properties of crosslinked PDA-PVAm and PDA-PAA copolymers were determined under in vitro conditions. Solutions of bile acids, glycocholic acid (GC) and glycochenodeoxycholic acid (GCDC), at different concentrations were prepared in N,N bis(hydroxyethyl)-2 aminoethane-sulfonic acid (BES) buffer. An appropriate amount of the polymer was taken in a preweighed 50 mL centrifuge tube. The weight of the polymer sample was corrected for loss on drying (which was measured by thermogravimetric analysis (TGA) method). To the polymer containing centrifuge tube was added appropriate amount bile acid solution. Additional BES buffer was added to this suspension to make the total volume to 40 mL. The suspension was vortexed for 1 minute and subsequently stirred for 3 hours at 50° C. At the end of this time the suspension was filtered using a 0.45 micro filter. The filtrate was analyzed by HPLC for its bile acid content, which corresponds to unbound bile acid. These unbound bile acid values were used to calculate bile acid binding capacities of the polymer hydrogels.

The substrate binding results for crosslinked PDA-PVAm copolymers are summarized in Table 4 below. The substrate binding results for crosslinked PDA-PAA copolymers are summarized in Table 5 below.

TABLE 4

In vitro Phosphate and Bile Acid Binding Properties of Crosslinked PDA-PVAm Copolymers

| Test Article | $PO_4$ Binding (mM/g) | GC Binding (mM/g) | GCDC Binding (mM/g) |
|---|---|---|---|
| Example 1-1-1 | 4.3 | 1.45 | 2.31 |
| Example 1-1-2 | 4.22 | 1.47 | 2.32 |
| Example 1-1-3 | 3.18 | 1.42 | 2.31 |
| Example 1-1-4 | 2.66 | 1.38 | 2.28 |
| Example 1-1-5 | 2.35 | 1.38 | 2.28 |
| Example 1-1-6 | — | 1.043 | 1.968 |
| Example 1-1-7 | — | 1.216 | 2.214 |
| Example 1-1-8 | — | 1.020 | 1.952 |

TABLE 4-continued

In vitro Phosphate and Bile Acid Binding Properties of Crosslinked PDA-PVAm Copolymers

| Test Article | $PO_4$ Binding (mM/g) | GC Binding (mM/g) | GCDC Binding (mM/g) |
|---|---|---|---|
| Example 1-1-9 | — | 1.340 | 2.319 |
| Example 1-1-10 | — | 0.937 | 1.584 |
| Example 1-1-11 | — | 1.340 | 2.247 |
| Example 1-1-12 | — | 0.673 | 1.055 |
| Example 1-1-13 | — | 0.818 | 1.475 |
| Example 1-1-14 | — | 0.702 | 1.257 |
| Example 1-1-15 | — | 0.918 | 1.437 |
| Example 1-1-16 | — | 1.131 | 1.994 |
| Example 1-1-17 | — | 1.143 | 1.770 |
| Example 1-1-18 | — | 1.246 | 2.230 |
| Example 1-1-19 | — | 1.358 | 2.280 |
| Colesevelam · HCl | — | 0.77 | 1.64 |
| 4.5% Epichlorohydrin crosslinked PDA | 2.37 | 1.34 | 2.24 |
| 4.5% Epichlorohydrin crosslinked PVAm | 3.78 | 1.40 | 2.28 |

— indicates not tested

TABLE 5

In vitro Phosphate and Bile Acid Binding Properties of Crosslinked PDA-PAA Copolymers

| Test Article | $PO_4$ Binding (mM/g) | GC Binding (mM/g) | GCDC Binding (mM/g) |
|---|---|---|---|
| Example 1-2-1 | 4.54 | 1.03 | 1.94 |
| Example 1-2-2 | 3.32 | 1.16 | 1.53 |
| Example 1-2-3 | 3.64 | 0.61 | 0.68 |
| Example 1-2-4 | 6.49 | 1.9 | 2.45 |
| Example 1-2-5 | 4.05 | 0.81 | 1.32 |
| Example 1-2-6 | 4.73 | 0.76 | 1.27 |
| Example 1-2-7 | 5.21 | 1.19 | 2.1 |
| Example 1-2-8 | 4.17 | 1.65 | 2.38 |
| Example 1-2-9 | 3.85 | 1.29 | 2.27 |
| Example 1-2-10 | 2.93 | 0.65 | 0.67 |
| Example 1-2-11 | 5.17 | 1.86 | 2.42 |
| Example 1-2-12 | 3.31 | 0.9 | 1.54 |
| Example 1-2-13 | 4.99 | 1.2 | 2.17 |
| Example 1-2-14 | 5.16 | 0.84 | 1.28 |
| Example 1-2-15 | 3.30 | 0.75 | 0.97 |
| Example 1-2-16 | 7.04 | 1.81 | 2.43 |
| Example 1-2-17 | 4.10 | 0.94 | 1.73 |
| Example 1-2-18 | 4.50 | 1.6 | 2.39 |
| Example 1-2-19 | 3.81 | 1.09 | 1.77 |
| Colesevelam · HCl | — | 0.77 | 1.64 |
| 4.5% Epichlorohydrin crosslinked PDA | 2.37 | 1.34 | 2.24 |

— indicates not tested

Example 3

In Vivo Studies

Example 3

1: In Vivo Phosphate Binding Properties of Crosslinked PDA-PVAm and PDA-PAA Copolymers After a week of acclimation to the facility, male Sprague Dawley rats (n=6) were transferred to metabolic cages to separate urine and feces. Animals were presented a chow diet plus a predetermined amount of the polymer. The control group was given no drug. The fecal material was collected for 24 hours on day 3 or day 7 of treatment. The fecal material was freeze-dried and ground in an amalgamator to a uniform powder. The powdered material (1 g) was placed in the extraction cell and a solution of 100 mM NaOH in 80% aqueous methanol was used for extraction. The extraction process was carried out by keeping the sample and solvent at 100° C. under a pressure of 1500 psi. A portion (0.25 mL) of the extract was evaporated and reconstituted in bovine calf serum. The sample was then analyzed enzymatically for bile acid concentration using a colorimetric assay. The in vivo bile acid binding properties of different copolymers are presented in Table 6.

TABLE 6

Results from in vivo Bile Acid Binding Study of Crosslinked PDA-PVAm Copolymers

| Test Article | Dose (% of Diet) | Total Fecal Bile Acid in 24 hours after 3 days of Treatment |
|---|---|---|
| Control group | 0 | 21 |
| Example 1-1-1 | 0.2 | 44 |
| Example 1-1-2 | 0.2 | 42 |
| Example 1-1-3 | 0.2 | 34 |
| Example 1-1-4 | 0.2 | 41 |
| Example 1-1-5 | 0.2 | 45 |
| Colesevelam · HCl | 0.4 | 65 |
| 4.5% Epichlorohydrin crosslinked PDA | 0.4 | 80 |
| 4.5% Epichlorohydrin crosslinked PVAm | 0.4 | 95 |

Example 3

2: In Vivo Anti-Diabetic Properties of Crosslinked PDA-PVAm and PDA-PAA Copolymers Ten week old male lean (C57BL/6J) and obese, diabetic db/db mice (C57BL6/J) were housed in a temperature controlled room with a dark-light cycle of 12 hours each. One week after arrival at the animal facility, the animals were grouped as a group of 8 by separating db/db animals from the lean animals. The animals were put on a diet containing standard laboratory chow along with a high fat diet. The diets of the treatment group of animal were supplemented with the polymers as dry powder at different weight % of the diet. The animals were monitored for body weights and food intake every other day. Fed and semi-fasted blood glucose, HbA1c, and plasma insulin were measured before start of the experiment and at the end of the $2^{nd}$, $3^{rd}$, and $4^{th}$ weeks of treatment. The effect of treatment on blood glucose was measured and the results are summarized as difference in blood glucose concentration (mmol/L of blood) at the start of the study and at particular time point.

TABLE 7

In vivo Effect on Blood Glucose with Crosslinked PDA-PVAm Copolymers

| Test Article | Dose (% of diet) | Non-fasted blood glucose normalized to start date (Δ glucose, mmol/L ) Week 2 | Week 3 | Week 4 |
|---|---|---|---|---|
| Control | 0 | −0.2 | −0.5 | −1.7 |
| Example 1-1-4 | 1.2 | −3.2 | −3.2 | −3.5 |
| Example 1-1-3 | 1.2 | −3.8 | −2.2 | −5.3 |
| Example 1-1-1 | 1.2 | −3.4 | −3.4 | −4.5 |
| Sevelamer | 1.2 | −3.2 | −0.5 | −3.5 |
| Lingaliptin (DDP-4 inhibitor) | 3 mg/kg of body weight | −4.3 | −0.5 | −1.6 |

TABLE 8

In vivo Effect on Plasma Insulin with Crosslinked PDA-PVAm Copolymers

| Test Article | Dose (% of diet) | Non-fasted blood glucose normalized to start date (Δ glucose, mmol/L ) Week 2 | Week 3 | Week 4 |
|---|---|---|---|---|
| Control | 0 | — | — | −1.7 |
| Example 1-1-4 | 1.2 | — | | −1.5 |
| Example 1-1-3 | 1.2 | — | — | −1.9 |
| Example 1-1-1 | 1.2 | — | — | −4.6 |
| Sevelamer | 1.2 | — | — | −3.8 |

— indicates not tested

The in vivo effect of different compositions of crosslinked PDA-PAA copolymers on blood glucose of dbd/db mice with escalating dose of test articles are presented in FIG. 5. The animals were given increased dose of the compounds at two-week intervals (1 wt. % (day 0), 2 wt. % (day 14) and 3 wt. % (day 28) of diet).

The in vivo effect of different compositions of crosslinked PDA-PAA copolymers on blood HBA1C of dbd/db mice with escalating dose of test articles are presented in FIG. 6. The animals were given increased dose of the compounds at two-week intervals (1 wt. % (day 0), 2 wt. % (day 14) and 3 wt. % (day 28) of diet).

The in vivo effect of different compositions of crosslinked PDA-PAA copolymers on liver weight of dbd/db mice with escalating dose of test articles are presented in FIG. 7. The animals were given increased dose of the compounds at two-week intervals (1 wt. % (day 0), 2 wt. % (day 14) and 3 wt. % (day 28) of diet).

The in vivo effect of different compositions of crosslinked PDA-PAA copolymers on liver triglyceride contents of dbd/db mice with escalating dose of test articles are presented in FIG. 8. The animals were given increased dose of the compounds at two-week intervals (1 wt. % (day 0), 2 wt. % (day 14) and 3 wt. % (day 28) of diet).

Example 3

3: In Vivo Effect of Crosslinked PDA-PVAm and PDA-PAA Copolymers on Insulin Resistance The effect of polydiallylamine copolymers on improving insulin resistance (glucose homeostasis) was evaluated by an oral glucose tolerance test (OGTT) using diet induced obese (DIO) rats as the disease models. Male SPD rats of seven week age (Taconic, Denmark) were given a diet consisting of normal chow and high fat content diet. After feeding with this diet for 24 weeks, the animals were randomized based on body weight and whole body fat. Each treatment group contains 10 animals. The animals were placed individually in separate cages throughout the study period. Subsequently the animals were given the above food mixed with appropriate amounts of the polymers in the food for four weeks. At the end of the fourth week, OGTT was carried out. For OGTT, after subjecting to fasting for 16 hours, the animals were administered dextrose (1 g/kg) by oral route. Blood samples were collected one hour and immediately before dextrose treatment as well as at specific time intervals up to 4 hr after dextrose treatment. Serum glucose levels in the blood samples. The average blood glucose concentration (AUC) during the entire time course for each treatment group is presented in Table 9.

TABLE 9

In vivo Effect on Blood Glucose with Crosslinked PDA-PVAm and PDA-PAA Copolymers

| Test Article | Dose (% of diet) | [Blood Glucose]$_{average}$ (mmol/L*min)† |
|---|---|---|
| Control | 0 | 2154 |
| Example 1-1-2 | 1.2 | 2005 |
| Example 1-1-3 | 1.2 | 1982 |
| Example 1-1-3 + Lingaliptin | 1.2 + 3 mg/kg | 1827 |
| Colesevelam | 1.2 | 2112 |
| Linagliptin | 3 mg/kg | 1940 |

†Average blood glucose concentration from −60 minutes to +240 minutes, followed by oral glucose administration

Example 3

4: In Vivo Anti-Diabetic Properties of Crosslinked PDA-PVAm and PDA-PAA Copolymers Six week old obese, diabetic KKAy mice were housed in a temperature controlled room with a dark-light cycle of 12 hours each. One week after arrival at the animal facility, the animals were grouped as a group of 8. The animals were put on high fat diet for additional 3 weeks. When target level of blood glucose and HbA1c was achieved, the diet was supplemented with the polymers at different weight % of the diet. Animals were treated with polymer mixed diet for six weeks. The animals were monitored for body weights and food intake every other day. Fed and semi-fasted blood glucose, HbA1c, and plasma insulin were measured before start of the experiment and at the end of every week of treatment. The effect of treatment on blood glucose and HbA1c was measured and the results are summarized as difference in their values at the start of the study and at the end of seven weeks of treatment and presented in FIG. 10 and FIG. 11 below.

The invention claimed is:

1. A polydiallylamine block copolymer comprising a plurality of polymer chains, wherein each polymer chain is according to Formula (I):

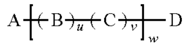

(I)

wherein:

u, and v are each independently an integer from 0 to 200,000; and w is an integer from 1 to 200,000;

A, B, C and D are each independently repeat units selected from Formula (II) or Formula (III);

wherein Formula (II) is according to the structural formula:

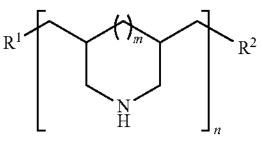

(II)

or a pharmaceutically acceptable salt thereof, wherein:

m is 0 or 1;

n is an integer from 1 to 200,000;

and Formula (III) is according to the structural formula:

(III)

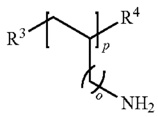

or a pharmaceutically acceptable salt thereof, wherein:

o is 0 or 1;

p is an integer from 1 to 200,000;

$R^1$ and $R^2$ and $R^3$ and $R^4$ are each independently selected from a group consisting of H, $(C_1\text{-}C_{10})$alkyl, $(C_2\text{-}C_9)$heteroalkyl, $(C_3\text{-}C_{10})$cycloalkyl, $(C_2\text{-}C_9)$heterocycloalkyl, $(C_6\text{-}C_{14})$aryl, $(C_2\text{-}C_9)$heteroaryl, $(C_1\text{-}C_{10})$alkylamine, —O(O)C—$(C_1\text{-}C_{10})$alkyl, $(C_1\text{-}C_{10})$alkyl-COOH, $(C_3\text{-}C_{10})$cycloalkyl-COOH, —(O)$CH_3$, —OH, amide, a guanidino group represented by Formula (A)

(A)

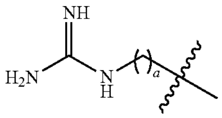

wherein a is an integer from 0 to 25, a guanidinium chloride group represented by Formula (B), (B)

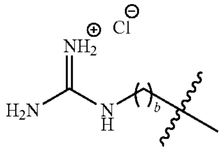

wherein b is an integer from 0 to 25, a guanidinobenzene group represented by Formula (C), (C)

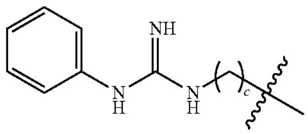

wherein c is an integer from 0 to 25, a dihydroxy group, represented by Formula (D), (D)

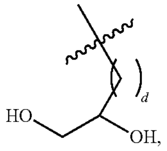

wherein d is an integer from 0 to 25, a polyethylene glycol group, represented by Formula (E)

(E)

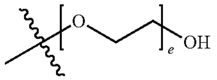

wherein e is an integer from 1 to 400, a group represented by Formula (F)

(F)

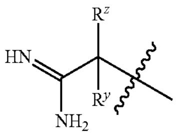

wherein $R^z$ and $R^y$ are each independently selected from the group consisting of H, $(C_1\text{-}C_{10})$alkyl, $(C_2\text{-}C_9)$heteroalkyl, $(C_3\text{-}C_{10})$cycloalkyl, $(C_2\text{-}C_9)$heterocycloalkyl, $(C_6\text{-}C_{14})$aryl, $(C_2\text{-}C_9)$heteroaryl, $(C_1\text{-}C_{10})$alkylamine, —O(O)C-$(C_1\text{-}C_{10})$alkyl, $(C_1\text{-}C_{10})$alkyl-COOH, $(C_3\text{-}C_{10})$cycloalkyl-COOH, —(O)$CH_3$, —OH and amide, a group represented by Formula (G)

(G)

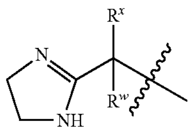

wherein $R^x$ and $R^w$ are each independently selected from the group consisting of H, $(C_1\text{-}C_{10})$alkyl, $(C_2\text{-}C_9)$heteroalkyl, $(C_3\text{-}C_{10})$cycloalkyl, $(C_2\text{-}C_9)$heterocycloalkyl, $(C_6\text{-}C_{14})$aryl, $(C_2\text{-}C_9)$heteroaryl, $(C_1\text{-}C_{10})$alkylannine, —O(O)C—$(C_1\text{-}C_{10})$alkyl, $(C_1\text{-}C_{10})$alkyl-COOH, $(C_3\text{-}C_{10})$cycloalkyl-COOH, —(O)$CH_3$, cyano, cyano$(C_1\text{-}C_{10})$alkyl, —OH and amide, and a point of attachment to another repeat unit of the copolymer;

and wherein:

(a) each polymer chain must be cross-linked with at least one other polymer chain, and (b) each polymer chain may be internally cross-linked; and wherein the molar ratio of Formula (II) monomer:Formula (III) monomer in the polydiallylamine copolymer is from 99:1 to 1:99, and the ratio of cross-linked repeat units:un-cross-linked repeat units is from 1:99 to 50:50.

2. The copolymer according to claim 1, wherein each m is 0.

3. The copolymer according to claim 1, wherein each m is 0 and each o is 1.

4. The copolymer according to claim 1, wherein the ratio of Formula (II) monomer:Formula (III) monomer is from 90:10 to 5:95.

5. The copolymer according to claim 1, wherein the copolymers has been cross-linked with a cross-linking agent.

6. The copolymer according to claim 5, wherein the cross-linking agent is selected from epichlorohydrin, epibromohydrin, (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1-bromo-2-chloroethane, 1,3-dibromopropane, bis(2-chloroethyl) amine, tris(2-chloroethyl)amine, and bis(2-chloroethyl) methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol digylcidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy) diphenylmethane, bisphenol F diglycidyl ether, 1,4-bis(2',3'-epoxypropyl)perfluoro-n-butane, 2,6-di(oxiran-2-ylmethyl)-1, 2,3,5,6,7-hexahydropyrrolo[3,4-f]isoindol-1,3,5,7-tetraone, bisphenol A diglycidyl ether, ethyl 5-hydroxy-6,8-di(oxiran-2-ylmethyl)-4-oxo-4h-chromene-2-carbo xylate, bis[4-(2,3-epoxy-propylthio) phenyl]-sulfide, 1,3-bis (3-glycidoxypropyl)tetramethyldisiloxane, 9,9-bis[4-(glycidyloxy) phenyl]fluorene, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris [[3-(epoxypropoxy)propyl]dimethylsilyloxy]-1, 3,5,7,9,11,14-heptacyclopentyltricyclo[7.3.3.15,11]heptasiloxane, 4,4'-methylenebis(N, N-diglycidylaniline), bis(halomethyl) benzene, bis(halomethyl)biphenyl and bis(halomethyl) naphthalene.

7. The copolymer according to claim 6, wherein the cross-linking agent is epichlorohydrin.

* * * * *